United States Patent [19]

Myers

[11] Patent Number: 5,488,131
[45] Date of Patent: Jan. 30, 1996

[54] SYNTHESIS OF COMPOUNDS WITH PREDETERMINED CHIRALITY

[75] Inventor: Andrew G. Myers, Pasadena, Calif.

[73] Assignee: California Institute of Technology

[21] Appl. No.: 216,926

[22] Filed: Mar. 23, 1994

[51] Int. Cl.$^6$ .................... C07C 271/00; C07C 233/04
[52] U.S. Cl. .................... 560/3; 560/25; 560/31; 560/33; 560/24; 560/27; 560/40; 564/182; 564/188; 564/189; 564/192; 564/193; 564/194; 564/199; 564/200; 564/202; 564/213; 564/215
[58] Field of Search .................... 564/202, 182, 564/188, 189, 192, 193, 194, 199, 200, 213, 215; 560/24, 27, 40, 25, 31, 32, 33

OTHER PUBLICATIONS

Caine, D., "Alkylations of Enols and Enolates", in *Comprehensive Organic Synthesis*, Trost, B. M.; Fleming, I., eds.; Pergamon Press: New York, 1991; 1 p. 1.

Crosby, D. A., "Synthesis of Optically Active Compounds: A Large Scale Perspective", in *Tetrahedron* 1991, 47, 4789.

Evans, D., "Stereoselective Akylation Reactions of Chiral Metal Enolates" in *Asymmetric Synthesis*, Academic Press, Inc.; 1984; 3, 1.

Larcheveque, M. et al., "Asymmetric Synthesis of α-Substituted Ketones and Acids via Chiral N, N-Substituted Amides" *Tetrahedron Lett.* 1978, 19, 3961.

Larcheveque et al., "Asymmetric Alkylation of Chiral N, N-Disubstituted Amides", *Organomet Chem.* 1979, 177, 5.

Evans, D. et al., "Enantioselective Akylatino of Chiral Enolates", *Tetrahedron Lett.* 1980, 21, 4233.

Sonnet, P. E. et al., "Asymmetric Alkylation of Amide Anions. Product Analysis by GLC Using Cholesteryl Cinnamate, a Liquid Crystal Phase", *J. Org. Chem.*, 1980, 45, 3137.

Kawanami, Y. et al., "Asymmetric Alkylation of Carboxyamides By Using trans-2, 5-Disubstituted Pyrrolidines as Chiral Auxiliaries", *Tetrahedron Lett.*, 1984, 25, 857.

Enomoto M. et al., "A Highly Effective Asymmetric Synthesis of α-Hydroxy Acids by Alkylation of Chiral N-(Benzyloxyacetyl)-TRANS-2, 5-Bis(Methoxymethoxymethyl) Pyrrolidine", *Tetrahedron Lett.*, 1985, 26, 1343.

Ikegami, S. et al., "Asymetric Synthesis of α-Amino Acids by Alkylation of a Glycine Amide Derivative Bearing Chiral 2,5-Disubstituted Pyrrolidine as an Amine Component" *Tethrahedron Lett.*, 1986, 27, 3403.

Soai, K. et al., "Asymmetric Synthesis Using Chiral Piperazine. I. Asymmetric Synthesis of 2–Substituted Alcohol and Carboxylic Acid by Diastereoselective Akylation of Chiral Diamides Derived From Piperazines", *Bull. Chem. Soc. Jpn.* 1987, 60, 3450.

Ikegami, S. et al., "Asymmetric Synthesis of α–Amino Acids by Akylation of N[N-Bis(Methylathio) Methylenegylcyl]–2–5 Bis(Methoxymethoxymethyl) Pyrrolidine and Enantioselective Synthesis of Protected (2S,9S)-2–Amino-8- Oxo-9,10–Epoxydecanoic Acid", *Tetrahedron*

1988, 44, 5333.

Juaristi E. et al., "Enantioselective Synthesis of β–Amino Acids. 4. 1,2 Asymmetric Induction in the Alkylation of 1–Benzoyl-3,6(S)–dimethylperhydropyrimidin–4–one. Preparation of the Like and Unlike Stereoisomers of 2–Methyl–and 2–Benzyl–3(s)–aminobutonic Acid" *J. Org. Chem.* 1993, 58, 2282.

Tamion, R. et al., "Asymmetric Synthesis of New Chiral Auxiliaries Derived From Isosorbide", *Tetrahedron: Asymmetry*, 1993, 4, 2415.

Schanen, V. et al., "Asymmetric Synthesis. XXXI. Synthesis of 2–Substituted Piperazines From Chiral Non–racemic Lactams", *Tetrahedron Lett.*, 1994, 35, 2533.

Micouin, L. et al., "Asymmetric Synthesis. XXXI. Synthesis of 3–substituted Piperidines from Chiral Non-racemic Lactams" *Tetrahedron Lett.*, 1994, 35, 2529.

Gennari, C. et al., "Asymmetric Electrophilic Amination: Synthesis of α–Amino and α–Hydrazino Acids With High Optical Purity", *J. Am. Chem. Soc.*, 1986, 108, 6394.

Pearson, W. et al., "Spiro Asymmetric Induction. Synthesis of Optically Pure α–Hydroxy Acid Derivatives by Alkylation of a Chiral Glycolate Enolate" *J. Org. Chem.*, 1986, 51, 3746.

Fuji, K. et al., "Binaphthol as a Chiral Auxiliary. Asymmetric Alkylation of Arylacetic Acid", *Tetrahedron Lett.*, 1989, 30, 2825.

Ihara, M. et al., "Stereoselective Alkylation of Dianions derived from Chiral Half–Esters of Monosubstituted Malonic Acids: Asymmetric Synthesis of α–Alkyl α–Amino Acids and Key Synthetic Intermediates of Hunteria and Aspidosperma Indole Alkaloids", *J. Chem. Soc. Perkin Trans.* 1991, 1, 525.

Jiang, Y. et al., "Asymmetric Synthesis XIII: The Stereocontrolled Synthesis of (R)–α–Amino Acids Via A Double Chiral Induction", *Synthetic Communications*, 1991, 21, 1087.

Williams, R. et al., "Asymmetric Synthesis of Monosubstituted and α,α–Disubstituted α–Amino Acids via Diastereoselective Glycine Enolate Alkylations", *J. Am. Chem. Soc.*, 1991, 113, 9276.

Meyers, A. et al., "Asymmetric Synthesis of R and S α–Alkylalkanoic Acids for Metalation and Alkylation of Chiral 2–Oxazolines", *J. Am. Chem. Soc.*, 1976, 98, 567.

Lutomski, K. et al., "Asymmetric Synthesis via Chiral Oxazolines", *Asymmetric Synthesis*, Morrison, J. D. ed.; Academic Press, New York, 1984, 3, 213.

(List continued on next page.)

*Primary Examiner*—Shailendra Kumar
*Attorney, Agent, or Firm*—Graham & James

[57] ABSTRACT

A method for synthesizing enantiomerically enriched chemical intermediates with predetermined chirality is described. The method comprises formation of a pseudoephedrine amide, followed by stereoselective alkylation at the alpha carbon. The chiral auxiliary can then be cleaved off, affording chiral end products useful for further transformations. The enantiomeric enrichment of the chiral end products may exceed 98%, and the chiral auxiliary can be recovered. Novel amides of pseudoephedrine used in this method are also disclosed.

3 Claims, No Drawings

OTHER PUBLICATIONS

Evans, D. et al., "Asymmetric Akylation Reactions of Chiral Imide Enolates. A Practical Approach to the Enantioselective Synthesis of a α–Substituted Carboxylic Acid Derivatives", *J. Am. Chem. Soc.*, 1982, 104, 1737.

Evans, D. et al., "Asymmetric Acylation Reaction of Chiral Imide Enolates. The First Direct Approach to the Construction of Chiral β–Dicarbonyl Synthons", *J. Am. Chem. Soc.*, 1984, 106, 1154.

Alexander, R. et al., "Asymmetric Alkylation and Sulphenylation of chiral O–Silylated Imide Enolates", *Tetrahedron Lett.*, 1985, 26, 5339.

Evans, D. et al., "Asymmetric Oxygenation of Chiral Imide Enolates. A General Approach to the Synthesis of Enantiomerically Pure α–Hydroxy Carboxyl Acid Synthons", *J. Am. Chem. Soc.*, 1985, 107, 4346.

Evans, D. et al., "Stereoselective Amination of Chiral Enolates. A New Approach to the Asymmetric Synthesis of α–Hydrazino and α –Amino Acid Derivatives", *J. Am. Chem. Soc.*, 1986, 108, 6395.

Trimble L. et al., "Amination of Chiral Enolates by Dialkyl Azodiformates, Synthesis of α–Hydrazino Acids and α–Amino Acids", *J. Am. Chem. Soc.*, 1986, 108, 6397.

Evans, D. et al., "Asymmetric Halogenation of Chiral Imide Enolates. A General Approach to the Synthesis of Enantiomerically Pure α– Amino Acids", *Tetrahedron Lett.*, 1987, 28, 1123.

Evans, D. et al., "Asymmetrc Synthesis of Anti–β–Hydroxy–α–Amino Acids", *Tetrahedron Lett.*, 1987, 28, 39.

Evans, D. et al., "The Asymmetric Synthesis of α–Amino Acids. Electrophilic Azidation of Chiral Imide Enolates, a Practical Approach to the Synthesis of (R)– and (S)–α–Azido Carboxylic Acids", *J. Am. Chem. Soc.*, 1990 112, 4011.

Yan, T. et al., "Asymmetric Alkylation Reactions of Camphor–Based Imide Enolate", *Tetrahedron Lett.*, 1991, 32, 4959.

Fadel, A., "Optically Active Arylpropionic Acids from the Stereoselective Alkylation of Chiral Imide Enolates", *Synlett*, 1992, 48.

Ahn, K. et al., "Diastereoselective Alkylation Reactions Employing a Camphor–Based Chiral Oxazinone Auxilliary", *Tetrahedron Asymmetry*, 1993, 4, 2435.

Drewes, S. et al., "Ephedrine–Derived Imidozolidin–2–ones. Broad Utility Chiral Auxiliaries in Asymmetric Synthesis", *Chem. Ber.*, 1993, 126, 2663.

Davies, S. et al., "Bifunctional Chiral Auxiliaries 6: Alkylations of Enolates Derived from 1,3–Diacylimidazolidine–2–thiones and 1,3–Diacylimidazolidin–2–ones", *Tetrahedron: Asymmetry*, 1994, 5, 585.

Ojima, I. et al., "Asymmetric Alkylation of chiral β –Lactam Ester Enolates. A New Approach to the Synthesis of α–Alkylated α–Amino Acids", *J. Am. Chem. Soc.*, 1987, 109, 6537.

Negrete, G. et al., "Asymmetric Alkylations of N–Acyl Dihydropyrimidinones", *Tetrahedron: Asymmetry*, 1991, 1, 105.

Davies, S. et al., "Asymmetric Aldol and Alkylation Reactions Mediated by the "Quat" Chiral Auxiliary (R)–(–)–5–Methyl–3,3–Dimethyl–2–Pyrrolidinone", *Tetrahedron Lett.*, 1994, 35, 2373.

Baird, G. et al., "Stereochemical Control and Mechanistic Aspects of the Alkylation of $[\eta^{5-}$ $C_5H_5)Fe(L)(CO)$ (COCHR)]—Li + (L= $PPh_3$ $PPh_2NEtHd$ 2; R= Me,Et): X-Ray Crystal Structure $[\eta^{5-}C_5H_5)Fe(PPh_3(CO)\{COCH(Me)Et\}]$, *J. Chem, Soc. Chem Commun.*, 1983, 1202.

Baird, G. etl al., "Stereoselective Carbon—Carbon Bond Formation via Alkylation of $[\eta^{5-}C_5H_5)Fe(PPh_{3)CO(COMe=CHR)]}$ (R= Me, Pr^n , Ph): X-Ray Crystal Structure of (Z)– [$\eta$ $C_5H_5)Fe(PPh_3)(CO)(COMe= CHMe)$] ", *Chem Soc. Chem. Comm.*, 1984, 745.

Davies, S. et al., "Stereocontrolled Tandem Alkylations: Michael Additions and Subsequent Alkylations of α,β–Unsaturated Acyl Ligands bound to $[(\eta^5-C_5H_5)Fe(CO)(PPh_3)]$" *J. Che*

Liebeskind, L. et al., "A Practical Synthesis of α,β–Unsaturated Iron Acyls, Chiral Enoate Synthons", *Tetrahedron Lett.*, 1985, 26, 3075.

Liebeskind, L. et al., "Transformation of Chiral Iron complexes Used in Organic Synthesis. Reactions of $\eta^5$-$CpFe(PPh_3)(CO)COCH_3$ and Related Species Leading to a Mild Stereospecific Synthesis of β–Lactams *J. Am. Chem. Soc.*, 1986, 108, 6328.

Davies, S. et al., "Stereoselective Synthesis of Quaternary Carbon Centres", *J. Chem. Soc. Chem. Commun.*, 1986, 495.

Davies, S. et al., " Determination of the Absolute Configuration and Optical Purity of $[(\eta^5-C_5H_5)Fe(CO)(PPh_3)COMe]$; X-ray Crystal Structure of (R)–$\{\eta^5-C_5H_5$ )Fe(CO)(PPH_3)COCH_2CH_2O[(R)– menthyl]$\}$ *J. Chem. Soc. Chem. Commun.*, 1986, 607.

Davies, S. et al., "The Asymmetric Synthesis of β–Lactams, Stereocontrolled Asymmetric Tandem Michael Additions and Alkylations of α.β–Unsaturated Acyl Ligands Bound to the Chiral Auxiliary $[(\eta^5-C_5H_5$ *Tetrahedron Lett.*, 1986, 27, 3787.

Schmierer, R. et al., "Functional Groups at Concave Cites: Asymmetric Alkylation of Esters with Very High Stereoselectivity and Reversal of Configuration by Change of Solvent", *Agnew. Chem. Int. Ed. Engl.*, 1981, 20, 207.

Helmchen, G. et al., "Influence of Cation Complexing Solvent Additives and Functional Groups in Asymmetric Alkylations of Esters via Lithium Enolates", *Tetrahedron Lett.*, 1983, 24, 3213.

Helmchen, G. et al., "Preparation of Enantiomerically Pure Chiral Alcohols by Asymmetric Alkylation of Glycolates", *Agnew Chem. Int. Ed. Engl.*, 1984, 23, 60.

Oppolzer, W. et al., "Camphorsulfonamide–Shielded, Asymmetric 1,4–Additions and Enolate Alkylations; Synthesis of a Corn Rootworm Pheromone", *Helv. Chim. Acta.*, 1985, 68, 212.

Oppolzer, W. et al., "Asymmetric Alkylation of N–Acylsultams: A General Route to Enantiomerically Pure, Crystalline C(α,α)–Disubstituted Carboxylic Acid Derivatives", *Tetrahedron Lett.*, 1989, 30, 5603.

Josien, H. et al., "Asymmetric Synthesis of L–Diphenylalanine and L–9–Fluorenyglycine via Room Temperature Alkylations of a Sultam– Derived Glycine Imine", *Tetrahedron Lett.*, 1991, 32, 6547.

Hutchins, R. et al., "Aminoborohydrides as Reduging Agents. 1. Sodium (Dimethylamino) and (tert–Butylamino) borohydrides as Selective Reducing Agents", *J. Org. Chem.*, 1984, 49, 2438.

Fisher, G. et al., "Synthesis and Characterization of Lithium Aminoborohydrides: A new Class of Powerful Reducing Agents", *Tetrahedron Lett.*, 1992, 33, 4533.

Belokon, Y., et al., " General Method for the Asymmetric

Synthesis of α–Amino Acids via Alkylation of the Chiral Nickel (||) Schiff Base Complexes of Glycine and Alanine", *J. Chem. Soc. Perkin Trans.*, 1988, 305.

Fisher, G. et al., "Aminoborohydrides. 3. A Facile Reduction of Tertiary Amides to the Corresponding Amines and Alcohols in High Purity Using Lithium Aminoborohydrides. Sterically controlled Selective C–N or C–O Bond Clevage", *Tetrahedron Lett.*, 1993, 34, 1091.

Fuller, J. et al., "Lithium Alum. Hydride–N–Methylpyrrolidine Complex. 1. Synthesis and Reactivity of Lithium Aluminum Hydride–N– Methylpyrrolidine Complex. An Air and Thermally Stable Reducing Agent Derived from Lithium Aluminum Hydride", *Tetrahedron Lett.*, 1994, 35, 1515.

Brown, H. et al., "Selective Reductions. V. The Partial Reduction of Tertiary Amides by Lithium Di– and Triethoxyaluminohydrides— A New Aldehyde Synthesis via the Dimethylamides", *J. Am. Chem. Soc.*, 1964, 86, 1089.

SYNTHESIS OF COMPOUNDS WITH PREDETERMINED CHIRALITY

This invention relates to the production of chiral compounds which are useful intermediates in the synthesis of organic molecules for pharmaceutical and industrial applications. More particularly, this invention relates to a practical asymmetric synthesis of general application which employs either enantiomer of pseudoephedrine as a chiral auxiliary.

BACKGROUND OF THE INVENTION

Stereoisomerism is a well known phenomenon in organic chemistry. By definition, stereoisomers are compounds that have the same molecular formula and connectivity, yet differ in the spatial arrangement of their atoms. Enantiomers represent one class of stereoisomers. Enantiomers are pairs of molecules that exist as nonsuperimposable mirror images of one another. Those compounds which cannot be superimposed on their mirror images are also said to be chiral.

A common feature of most chiral organic compounds is the presence of one or more "stereogenic" or asymmetric carbon atoms within the molecule. This invention describes a method for the preparation of a wide variety of such asymmetric carbon centers with predetermined stereochemistry. This invention also relates to novel intermediates useful in the synthesis of a wide variety of compounds with predetermined chirality.

Enantiomers are identical with respect to certain physical properties, such as their melting and boiling points. However, they may display profound differences in their chemical properties, particularly within biological systems. For example, it is now believed that the teratogenic effects of the notorious tranquilizer thalidomide are due to only one enantiomer of the drug; the other enantiomer is believed to be a safe and useful tranquilizer devoid of teratogenic side effects. Consequently, the preparation of pharmaceutical agents as pure enantiomers, uncontaminated by an enantiomeric impurity, is now an overriding concern within the pharmaceutical industry.

One approach to the synthesis of enantiomerically enriched asymmetric compounds is to employ an asymmetric catalyst. For example, U.S. Pat. Nos. 5,189,177 and 4,943,635 refer to catalysts for the reduction of ketones to form optically active alcohols and are limited to the production of optically active alcohols. Another approach is to employ stoichiometric chiral auxiliaries. An advantage of the use of chiral auxiliaries is that they allow for the facile purification of products to a high degree of diastereomeric purity by contrast, it is often difficult to further enrich the products of a reaction employing an asymmetric catalyst.

Evans and co-workers have developed a method for the synthesis of enantiomerically enriched molecules that employs one of two chiral oxazolidinones as a "chiral auxiliary." [D. A. Evans et al., J. Am. Chem. Soc., 1982, 104 1737]. A chiral auxiliary provides an asymmetric environment that dictates the stereochemical outcome of a reaction in a predictable fashion and which, subsequent to the reaction in question, is ideally removed intact for reuse. Disadvantages of the Evans method include the following: (1) the chiral auxiliary is costly when obtained from commercial suppliers, and is difficult to synthesize; (2) the attachment of the chiral auxiliary is difficult relative to the invention disclosed herein; (3) the key step in the Evans method, the alkylation reaction, is restricted to reactive substrates, e.g., those that are allylic or benzylic, or which deliver a methyl group; (4) the products of the Evans alkylation reaction are less versatile with respect to subsequent transformations versus the invention disclosed herein.

Larcheveque and co-workers have developed a method for asymmetric synthesis that uses ephedrine as a chiral auxiliary. [Larcheveque et al., *Tetrahedron Lett.,* 1978, 3961; Larcheveque et al., *J. Organometallic Chem.,* 1979, 177, 5]. Although ephedrine is less expensive than the oxazolidinone chiral auxiliaries of Evans et al. (1982), the method of Larcheveque et al. is impractical because it employs a highly carcinogenic co-solvent. In addition, the method, as described by Larcheveque et al. does not lead to highly enantiomerically enriched end products.

The present invention discloses the use of pseudoephedrine as a chiral auxiliary for the preparation of a wide variety of highly enantiomerically enriched end products. Both enantiomers of pseudoephedrine are readily available in large quantities at prices making the asymmetric synthesis disclosed herein commercially practical. The disclosed asymmetric synthesis is useful for producing a wide variety of compounds with predetermined chirality that are useful as chemical intermediates. Chiral intermediates synthesized according to the present invention are useful for the preparation of highly enantiomerically enriched pharmaceutical agents.

SUMMARY OF THE INVENTION

A method for synthesizing enantiomerically enriched chemical intermediates with predetermined chirality is described. The method comprises formation of a pseudoephedrine amide, followed by stereoselective alkylation at the alpha carbon. The chiral auxiliary can then be cleaved off, affording chiral end products useful for further transformations. The enantiomeric excess of the chiral end products may exceed 98%, and the chiral auxiliary can be recovered. Novel amides of pseudoephedrine used in this method are also disclosed.

DETAILED DESCRIPTION

For the purposes of this invention, the following definitions apply:

Adduct—A molecule formed by the chemical addition of two species.

Asymmetric Center—an atom in a molecule about which there is no plane of symmetry.

Chiral Auxiliary—an asymmetric molecule which biases a chemical reaction to favor selective formation of one stereoisomer over another.

Chirality—the characteristic of a molecule by which it cannot be superimposed on its mirror image. A chiral molecule and its mirror image are enantiomers.

Diastereomer—stereoisomers other than enantiomers.

Enantiomer—one of a pair of isomeric molecules that are non-superimposable mirror images of one another.

Enantiomeric Excess—the predominance of one enantiomer over the other in a mixture of the two. The degree of enrichment is expressed as the percentage difference of the major enantiomer over the minor one.

Enantiomerically Enriched—when the amount of one enantiomer in a mixture exceeds the amount of the other.

Stereoisomers—Molecules which have the same molecular formula and connectivity, yet differ in the spatial arrangement of their atoms.

The method of this invention employs the chiral auxiliary pseudoephedrine, [α-(1-methylaminoethyl)benzyl alcohol]

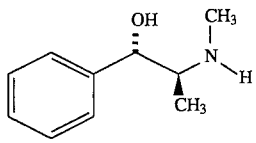

(+)-pseudoephedrine

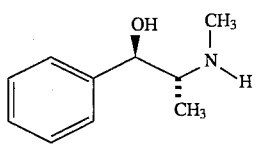

(−)-pseudoephedrine

Either the (1S,2S) or (1R,2R) enantiomers of pseudoephedrine may be used as the chiral auxiliary.

In one embodiment, this invention comprises a method of general application for synthesis of a wide variety of compounds of predetermined chirality that are useful in asymmetric synthesis. Briefly, this method involves the acylation of a given enantiomer of pseudoephedrine, followed by alkylation of the alpha carbon of the adduct. The alkylation proceeds in a stereoselective manner and is directed by the chiral auxiliary pseudoephedrine. The amide is transformed into the corresponding chiral carboxylic acid, primary alcohol, aldehyde or ketone, and the chiral auxiliary is recovered.

More specifically, in the first step of this method a carboxylic acid anhydride or carboxylic acid halide or other active acylating agent is condensed with the pseudoephedrine chiral auxiliary to form an amide of pseudoephedrine.

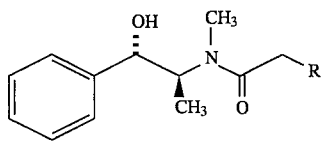

(S, S) Pseudoephedrine Amide

The substituent "R" is almost infinitely variable. It is expected that compounds where R is $(CH_2)_nCH_3$ and n is 0–14; R is branched alkyl, R is aromatic (e.g., phenyl, napthyl, heteroaromatic); R is alkenyl and R includes a heteroatom such as O,N,P,S or halogen, can be used. These pseudoephedrine amides are novel compounds, both in racemic and in enantiomerically enriched forms.

For example, the carboxylic acid anhydrides propionic anhydride and hexanoic anhydride were used to synthesize pseudoephedrine propionamide and pseudoephedrine hexanamide, respectively. Methods for the acylation of pseudoephedrine with a wide variety of compounds are known to those ordinarily skilled in synthetic organic chemistry.

In a second step, the pseudoephedrine amide is alkylated at the alpha carbon. Preliminarily, the pseudoephedrine amide is enolized using lithium diisopropylamide at low temperature in tetrahydrofuran. Other bases may be used in place of lithium diisopropylamide, for example, lithium dicyclohexylamide, lithium diethlamide, lithium hexamethyldisilazide, sodium hexamethyldisilazide and potassium hexamethyldisilazide.

It is believed that the factors responsible for the high diastereoselectivity of these alkylations are 1) the highly selective formation of a Z-configured enolate intermediate, and (2) the blocking of a specific π-face of this enolate (determined by the chirality of the pseudoephedrine employed) which leads to alkylation in a highly selective manner from the opposite π-face.

Alkylation is carried out in the presence of 6–10 equivalents of a lithium halide salt. Lithium chloride is preferred, although it is believed that other halide salts, including lithium bromide, and lithium iodide are also operative. It is further believed that other lithium salts may also be employed. The reaction may be carried out at from −78° C. to 0° C., the latter being preferred.

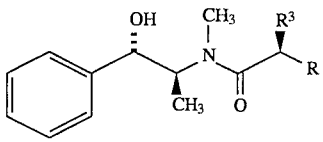

(S, S Alkylated Pseudoephedrine Amide)

Following extractive workup, the alkylated amides are purified by recrystallization or flash column chromatography to afford highly diastereomerically enriched products.

Fundamental to this method is the fact that the alkylation reaction produces essentially only one of the two possible isomers at the alkylation center; furthermore, it has been found that any contaminating isomer may be readily removed in a purification step. These products, "alkylated pseudoephedrine amides," are shown to be highly versatile intermediates, exemplified by their transformation into carboxylic acids, ketones, aldehydes, and primary alcohols of broad description. Because the latter transformations proceed without appreciable isomerization at the alkylation center, and because essentially only one configuration is produced at the alkylation center in the alkylation reaction, these carboxylic acid, ketone, aldehyde, and primary alcohol products are formed as highly enantiomerically enriched materials, thus establishing their utility as starting materials for asymmetric synthesis.

More generally, this invention comprises a process for preparing novel diastereomerically enriched compounds of the formula:

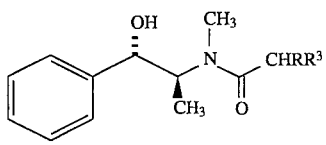

wherein R and $R^3$ are different and are each independently $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl which comprises reacting at about −78° C. to 0° C. a compound of the formula

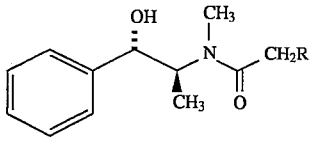

wherein R is defined above with a compound of the formula $R^3X^1$ wherein $R^3$ is as defined above and $X^1$ is a leaving group, such as a halide, in the presence of lithium salt and lithium dialkylamide or lithium, sodium, or potassium disilylamide base in a reaction inert solvent. In a preferred embodiment, the process occurs using lithium diisopropylamide at 0 degrees centigrade in the presence of a six-fold molar excess of lithium chloride.

This invention also comprises a process for preparing novel de (de=diastereomerically enriched) compounds of the form

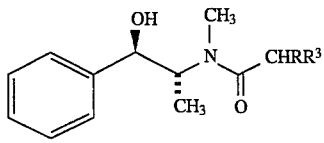

wherein R and $R^3$ are different and are each independently P(M) n where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from P(M) n where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl which comprises reacting at about −78° C. to 0° C. a compound of the formula

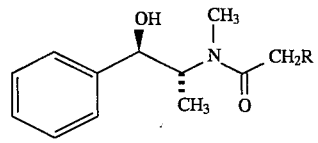

wherein R is as defined above with a compound of the formula $R^3X^1$ wherein $R^3$ is as defined above and $X^1$ is a leaving group, such as a halide, in the presence of lithium salt and lithium dialkylamide base in a reaction inert solvent. In a preferred embodiment, the process occurs at 0 degrees centigrade in the presence of a six-fold molar excess of lithium chloride.

This invention also comprises a process for preparing novel ee (ee=enantiomerically enriched) compounds of the form:

HOOCCHRR³ wherein R and $R^3$ are different and are each independently $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from P(M) n where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl $C_3$–$C_8$ cycloalkyl, $CO_2R^4$ and $NHCO_2R^4$ where $R^4$ is $C_1$–$C_{14}$ straight or branched-chain alkyl which comprises hydrolyzing a compound of the formula

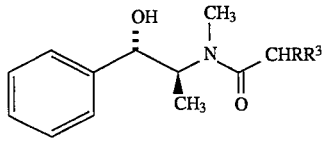

wherein R and $R^3$ are as defined above in the presence of a hydroxide in a reaction inert solvent. In a preferred embodiment, the hydroxide is tetrabutylammonium hydroxide.

This invention also comprises a process for preparation of novel ee compounds of the form:

HOOCCHRR³ wherein R and $R^3$ are different and are each independently $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where R is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl which comprises hydrolyzing a compound of the formula

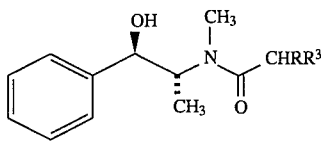

wherein R and $R^3$ are as defined above in the presence of hydroxide in a reaction inert solvent. In a preferred embodiment, the hydroxide is tetrabutylammonium hydroxide.

This invention also comprises a process for preparing novel ee compounds of the form:

$R^5CCHRR^3$ wherein R and $R^3$ are different and are each independently $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl and $R^5$ is $C_1$–$C_{14}$ straight or branched-chain alkyl, aryl, heteroaryl, $C_3$–$C_8$ cycloalkyl or $C_9$–$C_{16}$ bicycloalkyl wherein when $R^5$ is heteroaryl it is not bonded through the heteroatom which comprises reacting a compound of the formula

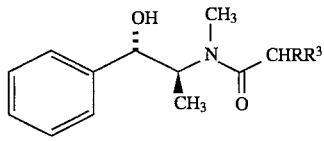

wherein R and $R^3$ are as defined above with $R^5X^2$ where $R^5$ is as defined above and $X^2$ is Li or a lanthanide at about −78° C. to 0° C. in a reaction inert solvent. In a preferred embodiment $R^5X^2$ reaction is added at about −78 degrees centigrade, and the mixture is subsequently warmed to 23° C.

This invention also comprises a process for preparing novel ee compounds of the formula:

$R^5CCHRR^3$ wherein R and $R^3$ are different and are each independently $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl and $R^5$ is $C_1$–$C_{14}$ straight or branched-chain alkyl, aryl, heteroaryl, $C_3$–$C_8$ cycloalkyl or $C_9$–$C_{16}$ bicycloalkyl wherein when $R^5$ is heteroaryl it is not bonded through the heteroatom which comprises reacting a compound of the formula

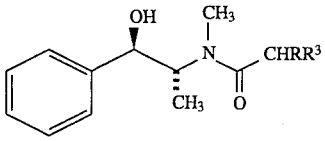

wherein R and $R^3$ are as defined above with $R^5X^2$ where $R^5$ is as defined above and $X^2$ is Li or a lanthanide at about −78° C. to 0° C. in a reaction inert solvent. In one embodiment the $R^5X^2$ at about −78 degrees centigrade, and the mixture subsequently warmed to about 23° C.

This invention also comprises a process for preparing novel ee compounds of the formula:

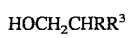
$HOCH_2CHRR^3$ wherein R and $R^3$ are different and are each independently $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl which comprises reacting a compound of the formula

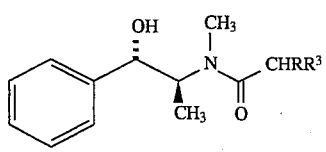

wherein R and R³ are as defined above with a secondary organic amine, (C₁–C₆) alkyllithium and borane in a reaction inert solvent at about 0° C. to 23° C. In a preferred embodiment, the secondary organic amine is pyrrolidine, the (C₁–C₆) alkyllithium is n-butyllithium and the reaction inert solvent is tetrahydrofuran.

This invention also comprises a process for preparing novel ee compounds of the formula:

HOCH₂CHRR³ wherein R is and R³ are different and are each independently P(M)$_n$ where M is O or C and n is 0,1,2 or 3, a C₁–C₁₄ straight or branched-chain alkyl group, a C₂–C₁₄ straight or branched-chain alkenyl or alkynyl group, C₁–C₆ alkoxy, C₁–C₆ alkylthio, halo, hydroxy, heteroaryl, C₃–C₈ cycloalkyl, C₉–C₁₆ bicycloalkyl, aryl or NR¹R² where R¹ and R² are each independently selected from the group consisting of hydrogen, C₁–C₆ straight or branched-chain alkyl, C₃–C₈ cycloalkyl, CO₂R⁴ and NHCO₂R⁴ where R⁴ is C₁–C₁₄ straight or branched-chain alkyl where the alkyl, alkenyl, alkynyl, alkoxy, alkylthio, heteroaryl, cycloalkyl, bicycloalkyl and aryl are optionally substituted with one or more groups independently selected from P(M)$_n$ where M is O or C and n is 0,1,2 or 3, a C₁–C₁₄ straight or branched-chain alkyl group, a C₂–C₁₄ straight or branched-chain alkenyl or alkynyl group, halo, C₁–C₆ alkylthio, heteroaryl, C₃–C₈ cycloalkyl, C₂–C₁₆ bicycloalkyl, aryl, hydroxy, C₁–C₆ alkoxy, thio, C₁–C₆ alkylthio, NR¹ R² where R¹ and R² are each independently selected from the group consisting of hydrogen, C₁–C₆ straight or branched-chain alkyl, C₃–C₈ cycloalkyl, CO₂R⁴ and NHCO₂R⁴ where R⁴ is C₁–C₁₄ straight or branched-chain alkyl which comprises reacting a compound of the formula

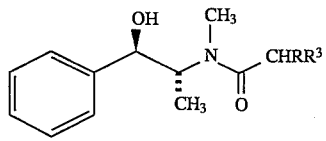

wherein R and R³ are as defined above with a secondary organic amine, (C₁–C₆) alkyllithium and borane in a reaction inert solvent at about 0° C. to 23° C. In a preferred embodiment, the secondary organic amine is pyrrolidine, the (C₁–C₆) alkyllithium is n-butyllithium and the reaction inert solvent is tetrahydrofuran.

This invention also comprises a process for preparing novel ee compounds of the formula:

O
‖
HCCHRR³ wherein R and R³ are different and are each independently P(M)$_n$ where M is O or C and n is 0,1,2 or 3, a C₁–C₁₄ straight or branched-chain alkyl group, a C₂–C₁₄ straight or branched-chain alkenyl or alkynyl group, C₁–C₆ alkoxy, C₁–C₆ alkylthio, halo, hydroxy, heteroaryl, C₃–C₈ cycloalkyl, C₉–C₁₆ bicycloalkyl, aryl or NR¹ R² where R¹ and R² are each independently selected from the group consisting of hydrogen, C₁–C₆ straight or branched-chain alkyl, C₃–C₈ cycloalkyl, CO₂ R⁴ and NHCO₂R⁴ where R⁴ is C₁–C₁₄ straight or branched-chain alkyl where the alkyl, alkenyl, alkynyl, alkoxy, alkylthio, heteroaryl, cycloalkyl, bicycloalkyl and aryl are optionally substituted with one or more groups independently selected from P(M)$_n$ where M is O or C and n is 0,1,2 or 3, a C₁–C₁₄ straight or branched-chain alkyl group, a C₂–C₁₄ straight or branched-chain alkenyl or alkynyl group, halo, C₁–C₆ alkylthio, heteroaryl, C₃–C₈ cycloalkyl, C₉–C₁₆ bicycloalkyl, aryl, hydroxy, C₁–C₆ alkoxy, thio, C₁–C₆ alkylthio, NR¹R² where R¹ and R² are each independently selected from the group consisting of hydrogen, C₁–C₆ straight or branched-chain alkyl, C₃–C₈ cycloalkyl, CO₂R⁴and NHCO₂R⁴ where R⁴ is C₁–C₁₄ straight or branched-chain alkyl which comprises reacting a compound of the formula

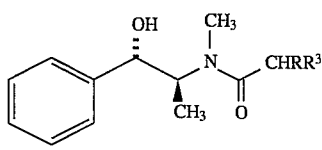

wherein R and R³ are as defined above with the product of a mixture of lithium aluminum hydride and ethyl acetate in a reaction inert solvent at about −78° C. to 0° C. In a preferred embodiment, the reaction inert solvent is hexanes or pentane.

This invention also comprises a process for preparing novel ee compounds of the formula:

O
‖
HCCHRR³ wherein R and R³ are different and are each independently P(M)$_n$ where M is O or C and n is 0,1,2 or 3, a C₁–C₁₄ straight or branched-chain alkyl group, a C₂–C₁₄ straight or branched-chain alkenyl or alkynyl group, C₁–C₆ alkoxy, C₁–C₆ alkylthio, halo, hydroxy, heteroaryl, C₃–C₈ cycloalkyl, C₉–C₁₆ bicycloalkyl, aryl or NR¹R² where R¹ and R² are each independently selected from the group consisting of hydrogen, C₁–C₆ straight or branched-chain alkyl, C₃–C₈ cycloalkyl, CO₂R⁴ and NHCO₂R⁴ where R⁴ is C₁–C₁₄ straight or branched-chain alkyl where the alkyl, alkenyl, alkynyl, alkoxy, alkylthio, heteroaryl, cycloalkyl, bicycloalkyl and aryl are optionally substituted with one or more groups independently selected from P(M)$_n$ where M is O or C and n is 0,1,2 or 3, a C₁–C₁₄ straight or branched-chain alkyl group, a C₂–C₁₄ straight or branched-chain alkenyl or alkynyl group, halo, C₁–C₆ alkylthio, heretoaryl, C₃–C₈ cycloalkyl, C₉–C₁₆ bicycloalkyl, aryl, hydroxy, C₁–C₆ alkoxy, thio, C₁–C₆ alkylthio, NR¹R² where R¹ and R² are each independently selected from the group consisting of hydrogen, C₁–C₆ straight or branched-chain alkyl, C₃–C₈ cycloalkyl, CO₂R⁴ and NHCO₂R⁴ where R⁴ is C₁–C₁₄ straight or branched-chain alkyl which comprises reacting a compound of the formula:

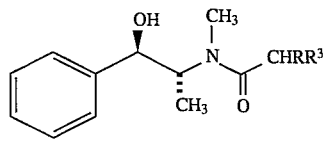

wherein R and R³ are as defined above with the product of a mixture of lithium aluminum hydride and ethyl acetate in a reaction inert solvent at about −78° C. to 0° C. In a preferred embodiment, the reaction inert solvent is hexanes or pentane.

This invention also comprises a process for the preparation of novel ee compounds of the form:

wherein R and $R^3$ are different and are each independently $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl $C_3$–$C_8$ cycloalkyl, $CO_2R^4$ and $NHCO_2R^4$ where $R^4$ is $C_1$–$C_{14}$ straight or branched-chain alkyl which comprises hydrolyzing a compound of the formula

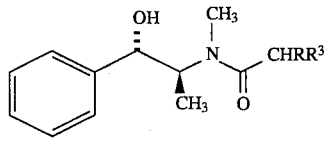

wherein R and $R^3$ are as defined above in the presence of acid and water in a reaction inert solvent. In a preferred embodiment, the process is conducted in the presence of sulfuric acid, dioxane and water.

This invention also comprises preparation of novel ee compounds of the form:

wherein R and $R^3$ are different and are each independently $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^2$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl which comprises hydrolyzing a compound of the formula

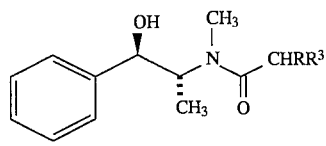

wherein R and $R^3$ are as defined above in the presence of acid and water in a reaction inert solvent. In a preferred embodiment, the process is conducted in the presence of sulfuric acid, dioxane and water.

In another embodiment, this invention, comprises novel compounds of the form:

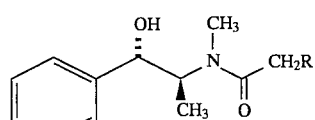

or

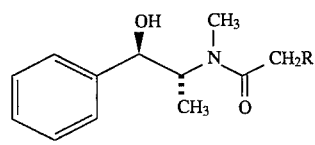

wherein R is $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl $CO_2R^4$ and $NHCO_2R^4$ where $R^4$ is $C_1$–$C_{14}$ straight or branched-chain alkyl, provided that R is not 1-(S)-methylpentyl or (R)-alpha-methylbenzyl. In a preferred embodiment, R is methyl, n-butyl, phenyl or benzyl.

In yet another embodiment of this invention, this invention comprises novel compounds of the form:

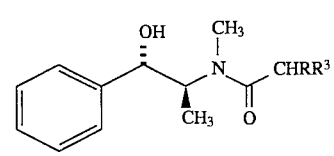

or

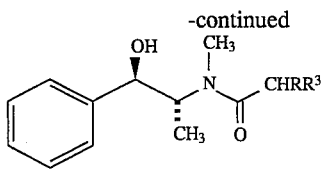

wherein R and $R^3$ are different and are each independently $P(M)_n$ where M is O or C and n is 0,1,2 or 3, a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from P(M) n where M is O or C and n is 0,1,2 or 3, a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl.

These novel compounds are useful in preparing compounds of predetermined chirality according to the method disclosed herein.

EXAMPLES

General Procedures

All nonaqueous reactions were performed in flame-dried glassware fitted with rubber septa under a positive pressure of argon, unless otherwise noted. Air-and moisture-sensitive liquids were transferred via syringe or stainless steel cannula. Deoxygenation of solutions was accomplished by either the freeze-pump-thaw technique, or evacuating and flushing the solution with argon. Organic solutions were concentrated on a Büchi rotary evaporator at 10–20 Torr, unless otherwise specified. Residual solvents were removed under an active vacuum of 0.5 Torr. Flash chromatography was performed using a forced flow with the indicated solvent using JT Baker silica gel (40 mm). Analytical thin-layer chromatography (TLC) was performed using Merck pre-coated silica gel 60 F-254 plates (0.25 mm, glass-backed, fluorescent at 254 nm).

Instrumentation

Melting points were recorded with a Büchi SMP-20 melting point apparatus and are uncorrected. Infrared spectra were recorded with a Perkin Elmer 1600 FTIR spectrometer. Data are represented as follows: frequency of absorption (cm-1), and intensity of absorption (s=strong, m=medium, w=weak, br=broad). The 1H NMR spectra were recorded on a General Electric QE-300 (300 MHz) NMR spectrometer; peaks are reported in ppm (δ scale), using the residual solvent peak as reference (CHCl3: 7.26, $C_6D5H$: 7.15). Data are represented as follows: chemical shift, multiplicity (s=singlet, d=doublet, t=triplet, q=quartet, qn=quintet, m=multiplet, br=broad), integration, coupling constants in Hertz. The 13C NMR were obtained on a QE-300 (75.5 MHz) NMR spectrometer, and are reported in ppm (δscale) using the solvent peak as reference (CDCl3: 77.0, $C_6D6$: 128.0).

Analytical gas-liquid chromatography (GC) was carried out on a Hewlett Packard 5890 gas chromatograph equipped with a splitless mode capillary injection system and a flame ionization detector, using a 25 m×0.25 mm Alltech Chirasil -Val III chiral fused silica capillary column.

Materials

Tetrahydrofuran and diethyl ether were distilled from sodium-benzophenone ketyl. Dichloromethane, hexanes, triethylamine, diisopropylamine, chlorotrimethylsilane, benzene, and toluene were distilled from calcium hydride. $C_6D6$ and CDCl3 were dried over activated 3 Å sieves. Solvents used in the workup and purification of compounds were HPLC-reagent grade or ACS grade and were used without further purification. Lithium chloride was dried under active vacuum for 4 h at 140° C., then transferred to a nitrogen-filled glovebox. The molarity of n-butyllithium was determined by titration with diphenylacetic acid. All alkyl halides were purified immediately prior to use by passage through a short column of basic alumina. All other reagents were used as received.

Method—Preparation of Pseudoephedrine Amides

Pseudoephedrine amides were prepared by condensing pseudoephedrine with the appropriate carboxylic acid anhydride or carboxylic acid chloride in tetrahydrofuran or dichloromethane.

Reaction with the carboxylic acid anhydride involved mixing the carboxylic acid anhydride with a tetrahydrofuran or dichloromethane solution of pseudoephedrine. It is preferred to keep the reaction in an ice bath or water bath since the reaction is exothermic. The pseudoephedrine amides were isolated by quenching the reaction with aqueous bicarbonate, and extracting the amide. Following removal of the solvent, recrystallization afforded analytically pure product.

Reaction with the carboxylic acid chloride involved adding the carboxylic acid chloride to a tetrahydrofuran or dichloromethane solution of pseudoephedrine and triethylamine at 0° C. The pseudoephedrine amides were isolated by quenching the reaction with water, and extracting the amide. Following removal of the solvent, recrystallization afforded analytically pure product.

EXAMPLE 1

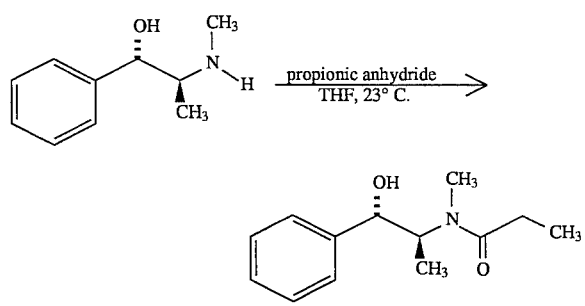

[S-[R*,R*]]-N-(2-hydroxy-1-methyl-2-phenylethyl)-N-methyl propionamide

Into a dry 1 L round-bottomed flask equipped with a magnetic stirrer was added (+)-pseudoephedrine (21.34 g, 129.1 mmol, 1.0 equiv) and tetrahydrofuran (250 mL). The flask was placed in a 23° C. water bath, and to the well-stirred solution was added propionic anhydride (17.98 g, 138.2 mmol, 1.07 equiv) in i mL portions over several minutes. The solution was stirred for an additional 10 min at 23° C., and then quenched with saturated sodium bicarbonate (400 mL), and stirred for 10 minutes. The reaction mixture was extracted with ethyl acetate (250 mL, 150 mL, 150 mL), and the combined organic extracts were dried over sodium sulfate. After the removal of the solvent under reduced pressure, a white solid was obtained. Recrystallization from toluene (125 mL) afforded the desired propionamide as white crystals (27.19 g, 95% yield): mp 114°–115° C.; 1H NMR (300 MHz, C6D6) δ6.95–7.45 (m, 5H), 4.83 (br, 1H), 4.51 (t, 1H, J=7.2 Hz), 4.0–4.2 (m, 2H), 3.6–3.75 (m, 1H), 2.77 (s, 3H), 2.40 (m, 2H), 2.06 (s, 3H), 1.73 (m, 2H), 1.22 (t,3H, J =7.3 Hz), 0.9–1.1 (m, 6H), 0.53 (d, 3H, J=6.7 Hz); 13C NMR (75.5 MHz, CDCl3) δ175.8, 174.8, 142.2, 141.5, 128.3, 128.1, 127.9, 127.4, 126.7, 126.3, 76.1, 75.0, 58.1, 57.7, 32.1, 27.3, 27.6, 26.6, 15.2, 14.2, 9.4, 9.0; FTIR (neat film) cm-1 3380 (br, m), 2979 (m), 1621 (s), 1454 (m), 1402 (m), 1053 (m), 702 (m); HRMS (FAB) Calcd for C13H20NO2 (MH+): 222.1495. Found: 222.1490; Anal. Calcd for C13H19NO2: C, 70.56; H, 8.65; N, 6.33. Found: C, 70.55; H, 8.50; N, 6.35.

EXAMPLE 2

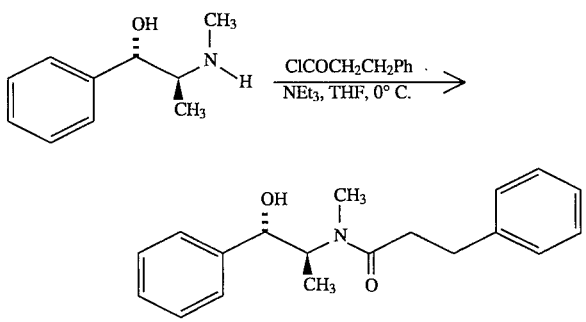

[S-[R*,R*]]-N-(2-hydroxy-1-methyl-2-phenylethyl)-N-methyl benzenepropionamide

Into a dry 1 L round-bottomed flask equipped with a magnetic stirrer was added (+)-pseudoephedrine (22.34 g, 135.22 mmol, 1.0 equiv), triethylamine (21.5 mL, 154 mmol, 1.14 equiv), and tetrahydrofuran (300 mL). The solution was cooled to 0° C. and hydrocinnamoyl chloride (25.08 g, 148.74 mmol, 1.1 equiv) in tetrahydrofuran (100 mL) was added via cannula over a 20 minute interval. After 30 minutes, the reaction was quenched with water. The amide was extracted from water (1 L) with ethyl acetate (400 mL, 120 mL, 120 mL), and the combined organic extracts were dried over sodium sulfate. After removal of the solvent under reduced pressure, a white solid was obtained, which was recrystallized from 2:1:1 ether/dichloromethane/hexanes (500 mL) affording the hydrocinnamide as white crystals (30.24 g, 75% yield): mp 102°–104° C.; 1H NMR (300 MHz, C6D6) δ7.0–7.4 (m, 5H), 4.59 (br, 1H), 4.48 (t, 1H, J=7.1 Hz), 4.20 (m, 1H), 4.01 (dd, 1H, J=8.4 Hz, 2.4 Hz), 3.66 (m, 1H), 3.15 (m, 2H), 2.93 (t, 2H, J=7.7 Hz), 2.79 (s, 3H), 2.49 (m, 2H), 2.13 (m, 2H), 2.02 (s, 3H), 0.92 (d, 3H, J=7.0 Hz), 0.49 (d, 3H, J=6.8 Hz); 13C NMR (75.5 MHz, CDCl3) δ174.3, 173.2, 142.2, 141.5, 141.3, 141.1, 128.6, 128.39, 128.36, 128.31, 128.29, 128.2, 127.6, 126.8, 126.4, 126.1, 125.9, 76.3, 75.3, 58.0, 36.1, 35.4, 32.3, 31.5, 31.1, 26.9, 15.2, 14.3; FTIR (neat film) cm-1 3374 (br, m), 3027 (m), 1621 (s), 1495 (m), 1454 (m), 1406 (m), 1118(m), 1048 (m), 753 (m), 701 (m); HRMS (FAB) Calcd for C19H24NO2 (MH+): 298.1808; Found: 298.1806.

EXAMPLE 3

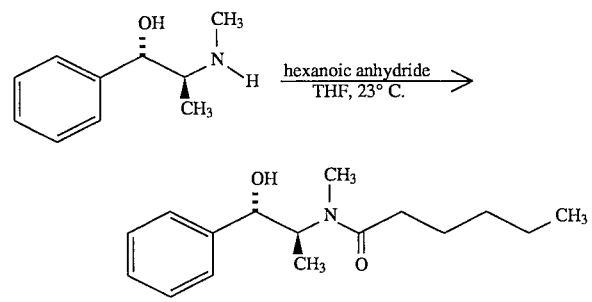

[S-[R*,R*]]-N-(2-hydroxy-1-methyl-2-phenylethyl)-N-methyl hexanamide

In a dry 2 L round-bottomed flask equipped with a magnetic stirrer was added (+)-pseudoephedrine (40.0 g, 242.06 mmol, 1.0 equiv) and tetrahydrofuran (500 mL), and the mixture was stirred in a 23° C. water bath. Hexanoic anhydride (55.51 g, 259 mmol, 1.07 equiv) was added via cannula over a 10 minute interval, and transfer was quantitated with an additional portion of tetrahydrofuran (10 mL). After 25 minutes, the reaction was quenched with saturated sodium bicarbonate (300 mL). Volatile components were removed under reduced pressure, and the residue was extracted from water (500 mL) with ethyl acetate (3×250 mL). The organic extracts were dried over sodium sulfate, and after removal of the solvent under reduced pressure, a white solid was obtained, which was recrystallized from 1:1 ether/hexanes (200 mL) to afford the hexanamide as white crystals (58.2 g, 91% yield): mp 62°–63° C.; 1H NMR (300 MHz, C6D6) δ7.0–7.4 (m, 5H), 4.9 (br, 1H), 4.52 (d, 1H, J=6.9 Hz), 4.14 (m, 1H), 3.77 (m, 1H), 2.79 (s, 3H), 2.42 (m, 2H), 2.13 (s, 3H), 1.83 (m, 2H), 1.59 (qn, 2H, J=7.6 Hz), 1.1–1.4 (m, 4H), 0.99 (d, 3H, J=7.0 Hz), 0.86 (t, 3H, J= 7.0 Hz), 0.59 (d, 3H, J=6.8 Hz); 13C NMR (75.5 MHz, CDCl3) δ175.2, 174.2, 142.3, 141.6, 128.3, 128.0, 127.8, 127.3, 126.7, 126.2, 76.1, 75.1, 58.2, 57.0, 34.1, 33.4, 32.4, 31.5, 31.3, 26.6, 24.9, 24.5, 22.31, 22.29, 15.2, 14.2, 13.82, 13.79; FTIR (neat film) cm-1 3378 (br, m), 2956 (m), 2931 (m), 2871 (m), 1618 (s), 1453 (m), 1406 (m), 1051 (m), 701 (m); HRMS (FAB) Calcd for C16H26NO2 (MH+): 264.1965. Found: 264.1966.

EXAMPLE 4

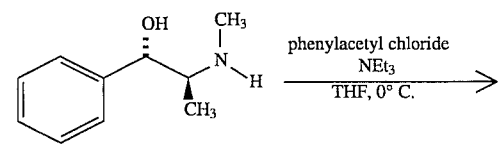

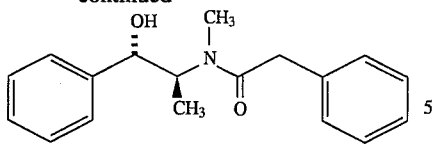

[S-[R*, R*]]-N-(2-hydroxy-1-methyl-2-phenylethyl)-N-methyl benzeneacetamide

A dry 1 L round-bottomed flask equipped with a magnetic stirrer was charged (+)-pseudoephedrine (13.92 g, 84.26 mmol, 1.0 equiv), triethylamine (13.39 mL, 96.06 mmol, 1.14 mmol), and tetrahydrofuran (340 mL). The solution was cooled to 0° C. and phenylacetyl chloride (14.33 g, 92.69 mmol, 1.1 equiv) was added via cannula over a 20 minute interval as a solution in tetrahydrofuran (90 mL). After 30 minutes, the reaction was quenched with saturated sodium bicarbonate. The amide was extracted from brine (1 L) with ethyl acetate (400 mL, 130 mL, 130 mL), and the organic extracts were dried over sodium sulfate. After removal of the solvent under reduced pressure, a solid was obtained. The solid was recrystallized from 2:1:1 ether/dichloromethane/hexanes (500 mL), affording the phenylacetamide (17.90 g, 75% yield) as a white powder: mp 145°–146° C.; 1H NMR (300 MHz, C6D6) δ6.9–7.5 (m, 10H), 4.55 (br, 1H), 4.48 (t, 1H, J=7.1 Hz), 4.11 (m, 1H), 3.95 (m, 1H), 3.83 (m, 1H), 3.78 (s, 2H), 3.31 (d, 2H, J=1.3 Hz), 2.76 (s, 3H), 2.12 (s, 3H), 0.95 (d, 3H, J=7.0 Hz), 0.42 (d, 3H, J=6.7 Hz); 13C NMR (75.5 MHz, CDCl3) δ173.1, 172.2, 142.2, 141.4, 135.5, 134.5, 128.7, 128.64, 128.58, 128.3, 128.1, 127.5, 126.73, 126.68, 126.6, 126.3, 76.2, 75.3, 58.6, 41.8, 41.4, 33.3, 27.0, 15.0, 14.3; FTIR (neat film) cm-1 3393 (br, m), 1618 (s), 1494 (m), 1453 (m), 1402 (m); HRMS (FAB) Calcd for C18H22NO2 (MH+): 284.1652. Found: 284.1646.

EXAMPLE 5

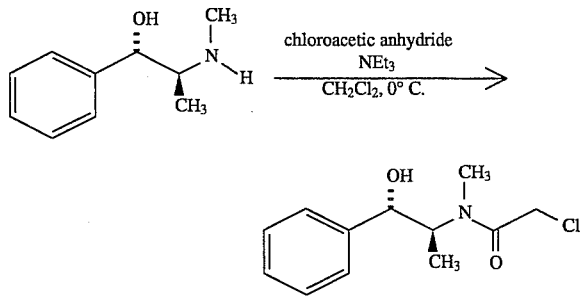

[S-(R*,R*)]-α-chloro-N-(2-hydroxy-1-methyl-2-phenylethyl)-N-methyl acetamide

In a dry round-bottomed flask equipped with a magnetic stirrer and an argon inlet was dissolved chloroacetic anhydride (5.00 g, 30.3 mmol, 1.0 equiv.) in dichloromethane (60 mL). The solution was cooled to 0° C. and a solution of (+)-pseudoephedrine (5.69 g, 33.3 mmol, 1.1 eq) and triethylamine (4.64 ml, 33.3 mmol, 1.1 eq) in dichloromethane (55 mL) was added via cannula. The reaction was stirred at 0° C. for 1 hr and was quenched by addition of water. A saturated solution of sodium bicarbonate was added and the resulting layers partitioned. The aqueous layer was back extracted with dichloromethane and the combined organic layers were dried over anhydrous sodium sulfate, filtered, and concentrated under reduced pressure. Purification of the residue by flash chromatography on silica gel with ethyl acetate/hexanes as the eluent (25%–75% gradient) gave [1S-( 1R*,2R*)-α-chloro-N-(2-hydroxy-1-methyl-2-phenylethyl)-N-methyl acetamide (6.60g, 90%) as an oil which crystallized on standing. Recrystallization from a minimum volume of ether gave analytically pure product (1:1 mixture of rotamers): mp 79°–81° C.; 1H NMR (300 MHz, CDCl3) δ7.28–7.41 (m, 5H), 4.54–4.63 (m, 1.5H), 4.35 (d, 0.5H, J=12.4 Hz), 4.07 (d, 0.5H, J=12.3 Hz), 4.07 (s, 1H), 3.98 (m, 0.5 H), 3.74 (d(br), 0.5H, J=4.7 Hz), 3.30 (d, 0.5H, J=3.2 Hz), 2.94 (s, 3H), 1.05 (d, 0.5H, J=6.6 Hz), 1.02 (d, 1.5H, J= 6.8 Hz); 13C NMR (75.5 MHz, CDCl3) δ168.2, 168.0, 141.6, 141.1, 128.7, 128.4, 127.9, 126.7, 126.5, 75.8, 75.1, 59.1, 57.7, 42.0, 41.7, 32.0, 27.4, 15.3, 14.0; FTIR (neat film) cm-1 3392, 3030, 2983, 1638. Anal. Calcd. for $C_{12}H_{16}ClNO_2$: C, 59.63; H, 6.67; N, 5.79 Found: C:59.61, H, 6.66; N, 5.76.

EXAMPLE 6

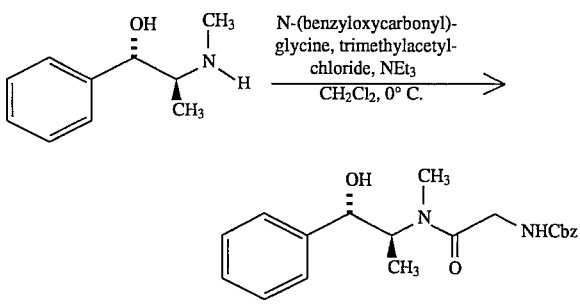

[S-(R*,R*)]-N2-(benzyloxycarbonyl)-N1-(2-hydroxy-1-methyl- 2-phenylethyl) -N1-methyl glycinamide In a dry round-bottomed flask equipped with a magnetic stirrer and an argon inlet was dissolved N (benzyloxycarbonyl)-glycine (5.00 g, 23.9 mmol, 1.0 equiv) in dichloromethane (25 mL). Triethylamine (3.66 mL, 26.3 mmol, 1.1 equiv) was added and the resulting mixture was cooled to 0° C. To the reaction was added dropwise trimethylacetylchloride (2.94 mL, 23.9 mmol, 1.0 equiv). A white precipitate formed and dichloromethane (25 mL) was added to allow efficient stirring. The reaction was stirred for 30 min at 0° C. and then a solution of (+)-pseudoephedrine (4.15 g, 25.1 mmol, 1.05 eq) and triethylamine (3.66 mL, 26.3 mmol, 1.1 eq) in dichloromethane (40 mL) was added via cannula. The reaction was stirred for 30 min at 0° C. Most of the solvent was removed under reduced pressure and water and saturated sodium bicarbonate were added. The product was extracted with two portions of ethyl acetate and the organic extracts were washed with saturated ammonium chloride. The combined organic extracts were dried over anhydrous sodium sulfate, filtered and concentrated under reduced pressure. Purification of the residue by flash chromatography on silica gel with ethyl acetate/hexanes as the eluent (30%–80% gradient) gave [S-(R*,R*)-N2-(benzyloxycarbonyl)-N 1-(2-hydroxy-1-methyl-2-phenylethyl)-N1-methyl glycinamide (6.67g, 78%) as a white foam (1:1 mixture of rotamers): 1H NMR (CDCl3, 300 MHz) δ7.25–7.40 (m, 10H), 6.04 (m, 1H), 5.09 (28, 4H), 4.67 (m, 0.5H), 4.51 (d, 0.5H, J=4.5 Hz), 4.49 (d, 0.5H, J=4.7 Hz), 4.23 (dd, 0.5H, J1 =16.7 Hz, J2=3.8 Hz), 4.15 (s(br), 1H), 4.04 (dd, 0.5H, J1=16.5 Hz, J2=5.1 Hz), 3.92 (d, 1H, J=4.3 Hz), 3.77 (m, 0.5H), 2.88 (s, 1.5H), 2.77 (s, 1.5H), 0.94 (d, 1.5H, J =6.4 Hz), 0.92 (d, 1.5H, J=6.3 Hz); 13C NMR (CDCl3, 75.5 MHz) δ169.3, 169.0, 156.2, 141.4, 141.1, 136.30, 136.26, 128.4, 128.2, 128.02, 127.95, 127.7, 126.6, 126.5, 75.2, 74.6, 66.5, 57.4, 56.1, 42.9, 42.6, 29.3, 26.8, 14.9, 13.9; FTIR (neat film) cm-1 3405, 3323, 3031, 2980, 1719, 1638.

Method—Alkylation of Pseudoephedrine Amides

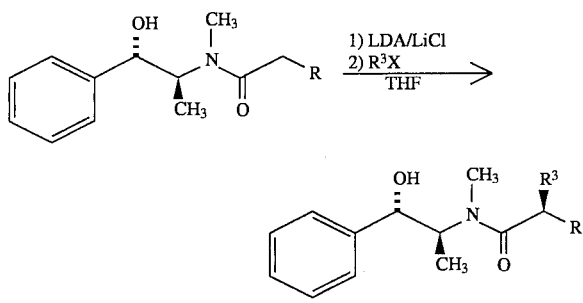

The novel process for alkylating pseudoephedrine amides comprised enolizing the amide with lithium diisopropylamide in tetrahydrofuran at −78°–23° C. over a period of about 1–2 hours, in the presence of lithium chloride (6–10 equiv). Reaction of the enolate with alkyl halides at 0° C., over a period of 30 minutes to 1 hour, afforded the alkylated amide. The alkylated amides were isolated by quenching the reaction with ammonium chloride, followed by extraction with ethyl acetate. The amides were then purified by recrystallization or flash column chromatography to afford highly diastereomerically enriched products.

EXAMPLE 7

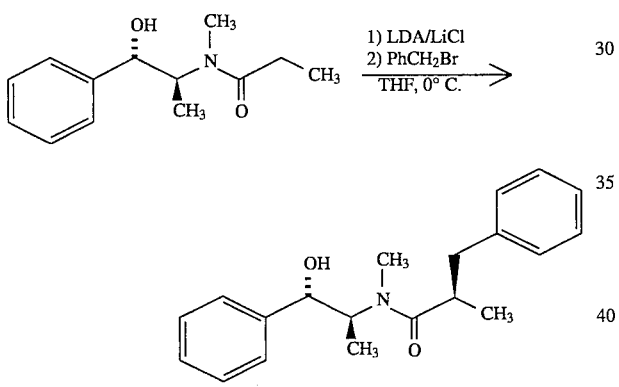

[1S-[1R*(S*), 2R*]]-N-(2-hydroxy-1-methyl-2-phenylethyl)-N, 2-dimethyl benzenepropionamide A dry 2 L 3-necked round-bottomed flask was equipped with a mechanical stirrer, and charged with lithium chloride (25.0 g, 596 mmol, 6.0 equiv), diisopropylamine (31.3 mL, 224 mmol, 2.25 equiv), and tetrahydrofuran (120 mL). The suspension was cooled to −78° C., and n-butyllithium (2.43M in hexanes, 85.1 mL, 207 mmol, 2.08 equiv) was added via cannula. After a brief warming to 0° C., it was recooled to −78° C. [S-[R*,R*]]-N-(2-hydroxy-1-methyl-2-phenylethyl)-N-methyl propionamide (22.0 g, 99.41 mmol, 1.0 equiv) was added as a 0° C. solution in tetrahydrofuran (300 mL). The resulting solution was stirred at −78° C. for 1 hour, warmed to 0° C. for 15 minutes, warmed to 23° C. for 5 minutes, and cooled to 0° C. Benzyl bromide (17.74 mL, 149 mmol, 1.5 equiv) was added, and the reaction was stirred at 0° C. The reaction was quenched after 15 minutes with saturated ammonium chloride, and the amide was extracted from saturated ammonium chloride (800 mL) with ethyl acetate (500 mL, 150 mL, 150 mL). The combined organic extracts were dried over sodium sulfate, and after removal of the solvent under reduced pressure, a yellow solid was obtained. Recrystallization from toluene (100 mL) yielded the desired product as a white powder (27.77 g, 90% yield). GC analysis of the TMS ether indicated a diastereomeric purity of the amide of greater than 99% de: mp 136°–137° C.; 1H NMR (300 MHz, C6D6) δ6.9–7.4 (m, 10 H), 4.45 (m, 1H), 4.25 (br, 1H), 3.96 (m, 1H), 3.80 (m, 1H), 3.36 (dd, 2H, J=13.1 Hz, 6.92 Hz), 3.01 (m, 1H), 2.75 (m, 1H), 2.70 (s, 3H), 2.45–2.59 (m, 3H), 2.08 (s, 3H), 1.05 (d, 3H, J=7.0 Hz), 1.02 (d, 3H, J=6.5 Hz), 0.83 (d, 3H, J=7.0 Hz), 0.59 (d, 3H, J=6.8 Hz); 13C NMR (75.5 MHz, CDCl3) δ178.2, 177.2, 142.3, 141.1, 140.5, 139.9, 129.2, 128.9, 128.6, 128.31, 128.26, 127.5, 126.8, 126.4, 126.2, 76.4, 75.2, 58.0, 40.3, 40.0, 38.9, 38.1, 32.3, 27.1, 17.7, 17.4, 15.5, 14.3; FTIR (neat film) cm-1 3384 (br, m), 3027 (m), 2973 (m), 2932 (m), 1617 (s), 1493 (m), 1453 (m), 1409 (m), 1080 (m), 1050 (m), 701 (s); HRMS (FAB) Calcd for C20H26NO2 (MH+): 312.1965. Found: 312.1972; Anal. Calcd for C20H25NO2: C, 77.14, H, 8.09, N, 4.50. Found: C, 76.87, H, 8.06, N, 4.50.

EXAMPLE 8

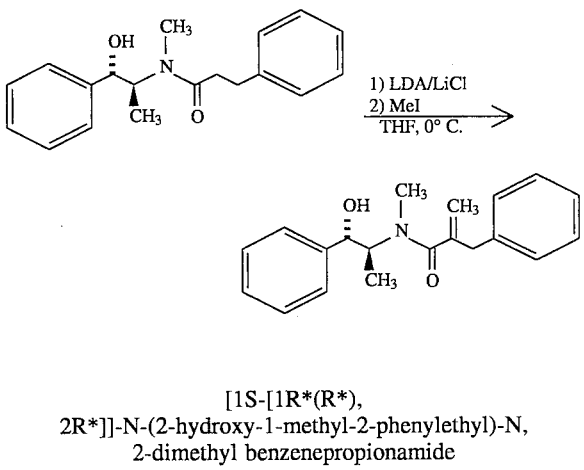

[1S-[1R*(R*), 2R*]]-N-(2-hydroxy-1-methyl-2-phenylethyl)-N, 2-dimethyl benzenepropionamide A dry 1 L 3-necked round-bottomed flask equipped with a mechanical stirrer was charged with lithium chloride (5.99 g, 141.22 mmol, 6.0 equiv), diisopropylamine (7.42 mL, 52.96 mmol, 2.25 equiv), and tetrahydrofuran (75 mL). The suspension was cooled to −78° C., and n-butyllithium (1.73M in hexanes, 28.30 mL, 48.96 mmol, 2.08 equiv) was added via cannula, and the resulting solution was briefly warmed to 0° C., then recooled to −78° C. [S-[R*,R*]]-N-(2-hydroxy-1-methyl- 2-phenylethyl)-N-methyl benzenepropionamide (7.0 g, 23.54 mmol, 1.0 equiv) was added at 0° C. as a solution in tetrahydrofuran (75 mL). The mixture was stirred at −78 ° C. for 1 h, 0° C. for 15 minutes, and 23° C. for 5 minutes, then recooled to 0° C. Iodomethane (4.40 mL, 70.61 mmol, 3.0 equiv) was added, and after 45 minutes, the reaction was quenched with saturated ammonium chloride. The amide was extracted from saturated ammonium chloride (400 mL) with ethyl acetate (3×140 mL), and upon removal of the solvent under reduced pressure a white solid was obtained. Recrystallization from 1:1 ether/hexanes (60 mL) provided the methylated hydrocinnamide as white crystals (5.89 g, 80% yield). GC analysis of the TMS ether indicated a diastereomeric purity of the amide of 93% de: mp 79°–81° C.; 1H NMR (300 MHz, C6D6) δ6.95–7.4 (m, 10 H), 5.25 (br, 1H), 4.51 (t, 1H, J=7.0 Hz), 3.97 (m, 1H), 3.75 (m, 1H), 3.15 (m, 1H), 3.06 (m, 1H), 3.02 (m, 2H), 2.71 (s, 3H), 2.58 (m, 1H), 2.4 (m, 2H), 1.93 (s, 3H), 1.34 (d, 3H, J=6.3 Hz), 1.00 (d, 3H, J=7.0 Hz), 0.93 (d, 3H, J=6.4 Hz), 0.30 (d, 3H, J=6.8 Hz); 13C NMR (75.5 MHz, CDCl3) δ178.1, 177.0, 142.3, 141.3, 140.2, 139.9, 128.94, 128.86, 128.6, 128.34, 128.29, 128.2, 127.4, 126.7, 126.3, 126.2, 126.1, 76.1, 75.4, 60.3, 41.2, 40.3, 39.0, 38.2, 33.9, 27.0, 18.2, 17.6, 14.8, 14.2; FTIR (neat film) cm-1 3374 (br, m), 2974 (m), 1614 (s), 1453 (m), 1080 (m), 756 (m), 701 (m); HRMS (FAB) Calcd for C20H26N02 (MH+): 312. 1965. Found: 312. 1965.

EXAMPLE 9

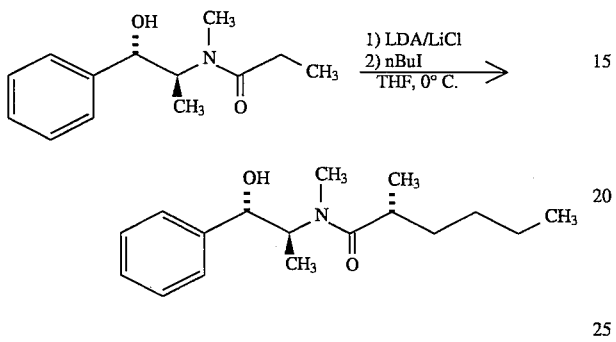

[1S-[1R*(S*), 2R*]]-N-(2-hydroxy-1-methyl-2-phenylethyl)-N, 2-dimethyl hexanamide A dry 2 L 3-necked round-bottomed flask equipped with a mechanical stirrer was charged with lithium chloride (16.81 g, 396.4 mmol, 6.0 equiv), diisopropylamine (20.83 mL, 148.6 mmol, 2.25 equiv), and tetrahydrofuran (175 mL). The suspension was cooled to −78° C., and n-butyllithium (1.73M in hexanes, 79.4 mL, 137.4 mmol, 2.08 equiv) was added via cannula, and the mixture briefly warmed to 0° C., and recooled to −78° C. [S-[R*,R*]]-N-(2-hydroxy-1-methyl-2-phenylethyl)-N-methyl propionamide (14.62 g, 66.06 mmol, 1.0 equiv) was added as a 0° C. solution in tetrahydrofuran (150 mL), and the reaction was stirred at −78° C. for 1 hour, 0° C. for 15 minutes, and 23° C. for 5 minutes, then cooled back to 0° C. Iodobutane (22.55 mL, 198.2 mmol, 3.0 equiv) was added, and after 90 minutes, the reaction was quenched with saturated ammonium chloride. The amide was extracted from saturated ammonium chloride (800 mL) with ethyl acetate (500 mL, 150 mL, 150 mL). The combined organic extracts were dried over sodium sulfate, and after removal of the solvent under reduced pressure a yellow solid was obtained. The solid was recrystallized from hexanes (100 mL) affording the butylated propionamide as white crystals (14.75 g, 80% yield). GC analysis of the TMS ether indicated a diastereomeric purity of the amide of greater than 99% de: mp 65.5°–66.5° C.: 1H NMR (300 MHz, C6D6) δ7.0–7.45 (m, H), 5.17 (br, 1H), 4.55 (t, 1H, J=7.2 Hz), 4.06 (m, 1H), 3.90 (m, 1H), 2.77 (s, 3H), 2.70 (m, 1H,), 2.22 (s, 3H), 2.17 (m, 1H), 1.70 (m, 2H), 1.40 (m, 1H), 1.02 (d, 3H, J= 7.2 Hz), 0.99 (d, 3H, J=6.8 Hz), 0.85 (3H, J=7.0 Hz), 0.9–1.25 (m, 9H), 0.62 (d, 3H, J=6.8 Hz); 13C NMR (75.5 MHz, CDCl3) δ179.2, 177.8, 142.6, 141.2, 128.6, 128.3, 128.2, 127.4, 126.8, 126.2, 76.4, 75.4, 59.1, 57.8, 36.5, 35.8, 33.7, 33.4, 29.7, 29.5, 22.9, 22.7, 18.0, 17.3, 15.3, 14.5, 14.1, 14.0; FTIR (neat film) cm-1 3382 (br, m), 2959 (m), 2932 (m), 2872 (m), 1614 (s), 1454 (m), 1109 (m), 701 (m); HRMS (FAB) Calcd for C17H28NO2 (MH+): 278. 2121. Found: 278. 2124.

EXAMPLE 10

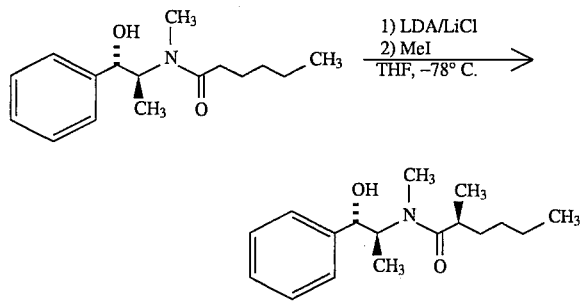

[1S-[1R*(R*), 2R*]]-N-(2-hydroxy-1-methyl-2-phenylethyl)N, 2-dimethyl hexanamide In a dry 1 L 3-necked round-bottomed flask equipped with a mechanical stirrer was charged lithium chloride (7.73 g, 182.2 mmol, 6.0 equiv), diisopropylamine (9.58 mL, 68.34 mmol, 2.25 equiv), and tetrahydrofuran (75 mL). The suspension was cooled to −78° C., and n-butyllithium (1.71M in hexanes, 36.94 mL, 63.17 mmol, 2.08 equiv) was added via cannula, and after a brief warming to 0° C., the suspension was recooled to −78° C. [S-[R*,R*]]-N-(2-hydroxy-1-methyl-2-phenylethyl)-N-methyl hexanamide (8.0 g, 30.37 mmol, 1.0 equiv) was added at 0° C. as a solution in tetrahydrofuran (50 mL), and the solution stirred at −78° C. for 1 hour, 0° C. for 15 minutes, and 23° C. for 5 minutes, and then recooled to −78° C. Iodomethane (5.67 mL, 91.11 mmol, 3.0 equiv) was added, and the reaction was quenched after 6 hours with methanol (7 mL, 5.7 equiv). Volatile components were removed by rotary evaporation, and the amide was extracted from saturated ammonium chloride (400 mL) with ethyl acetate (3×130 mL). The combined organic extracts were dried over sodium sulfate, and after removal of the solvent under reduced pressure, a yellow oil was obtained. The oil was purified by flash chromatography (50% ethyl acetate/hexanes) affording the methylated hexanamide (7.49 g, 89% yield) as a yellow oil. GC analysis of the TMS ether indicated a diastereomeric purity of the amide of 96% de. 1H NMR (300 MHz, C6D6) δ7.0–7.4 (m, 5H, 5.30 (br, 1H), 4.56 (t, 1H, J= 6.8 Hz), 4.16 (d, 1H, J=8.6 Hz), 3.95 (m, 1H), 2.82 (s, 3H), 2.70 (m, 1H), 2.18 (s, 3H), 1.78 (m, 2H), 1.1–1.4 (m), 1.33 (d, 3H, J=6.7 Hz), 1.08 (d, 3H, J=7.0 Hz), 1.0 (m, 3H), 0.92 (d, 3H, J=6.8 Hz), 0.87 (t, 3H, J=6.9 Hz), 0.69 (d, 3H, J=6.7 Hz); 13C NMR (75.5 MHz, CDCl3) δ: 178.9, 177.9, 142.5, 141.5, 128.5, 128.0, 127.3, 126.8, 126.1, 76.3, 75.2, 59.8, 57.9, 36.4, 35.5, 34.2, 33.6, 29.5, 27.0, 22.7, 17.6. 17.3, 15.5, 14.3, 13.9; FTIR (neat film) cm-1: 3382 (br, m), 2959 (s), 2932 (s), 1614 (s), 1470 (m), 1112 (m), 1087 (m), 1050 (m), 701 (m); HRMS (FAB) Calcd for C17H28NO2 (MH+): 278.2121 Found: 278.2119.

EXAMPLE 11

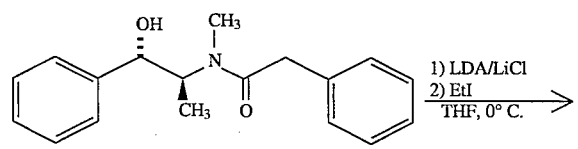

23

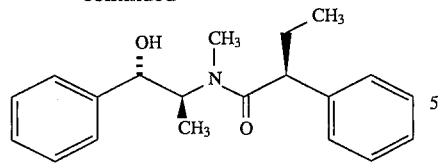

[1S-[1R*(R*),
2R*]]-α-ethyl-N-(2-hydroxy-1-methyl-2-
phenylethyl)-N-methyl benzeneacetamide A dry 500 mL round-bottomed flask was charged with lithium chloride (4.24 g, 100 mmol, 10.0 equiv), diisopropylamine (3.1 mL, 22.1 mmol, 2.21 equiv), and tetrahydrofuran (35 mL). The suspension was cooled to −78° C., and n-butyllithium (2.04M in hexanes, 10.20 mL, 20.8 mmol, 2.08 equiv) was added via cannula, and the mixture was briefly warmed to 0° C. and then recooled to −78° C. [1S-[1R*, 2R*]]-N-(2-hydroxy-1-methyl-2-phenylethyl)-N-methyl benzeneacetamide (2.83 g, 10.0 mmol, 1.0 equiv) was added as a solution in tetrahydrofuran (50 mL), and the mixture was stirred at −78° C. for 1 hour, 0° C. for 10 minutes, and 23° C. for 4 minutes, then cooled to 0° C. Ethyl iodide (3.2 mL, 40 mmol, 4.0 equiv) was added, and the reaction was quenched after 40 minutes with saturated ammonium chloride. The amide was extracted from saturated ammonium chloride (800 mL) with ethyl acetate (3×100 mL), and the combined organic extracts were dried over sodium sulfate. After removal of the solvent under reduced pressure, flash column chromatography (50% ethyl acetate/hexanes) of the oily residue afforded a colorless oil which slowly solidified (2.85 g, 92% yield). GC analysis of the TMS ether indicated a diastereomeric purity of the amide of greater than 98% de: mp 65°–66° C.; 1H NMR (300 MHz, C6D6) δ6.9–7.4 (m, 5H), 4.95 (br, 1H), 4.51 (t, 1H, J=6.9 Hz), 4.03 (m, 1H), 3.82 (m, 1H), 3.11 (dd, 1H, J=7.5 Hz, 7.0 Hz), 2.78 (s, 3H), 2.48 (m, 2H), 2.25 (m, 1H), 2.12 (s, 3H), 1.90 (m, 1H), 1.73 (m, 2H), 0.98 (d, 3H, J=6.8 Hz), 0.97 (m, 3H), 0.82 (t, 3H, J =7.3 Hz), 0.30 (d, 3H, J=6.5 Hz); 13C NMR (75.5 MHz, CDCl3) δ175.4, 174.2, 142.3, 141.3, 140.5, 139.6, 128.8, 128.7, 128.7, 128.3, 128.2, 127.8, 127.7, 127.4, 126.9, 126.7, 126.6, 126.3; FTIR (neat film) cm-1: 3384 (br, m), 3027 (m), 2966 (m), 2922 (m), 2873 (m), 1620 (s), 1491 (m), 1453 (m), 1406 (m), 761 (m), 701 (m); HRMS (FAB) Calcd for C20H26NO2 (MH+): 312. 1965. Found: 312. 1962.

EXAMPLE 12

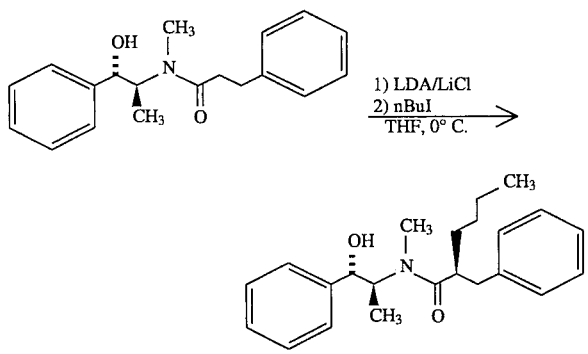

24

[1S-[1R*(R*),
2R*]]-α-butyl-N-(2-hydroxy-1-methyl-2-
phenylethyl)-N-methyl benzenepropionamide A dry 100 mL Schlenk flask was charged with lithium chloride (1.48 g, 35 mmol, 10 equiv), diisopropylamine (1.10 mL, 7.88 mmol, 2.25 equiv), and tetrahydrofuran (12 mL). The suspension was cooled to −78° C. and n-butyllithium (2.04M in hexanes, 3.57 mL, 2.08 equiv) was added, and the mixture was warmed briefly to 0° C., then cooled to −78° C. [S-[ R*,R*]]-N-(2-hydroxy-1-methyl-2-phenylethyl)-N-methyl benzene-propionamide (0.992 g, 3.5 mmol, 1.0 equiv) was added as a solution in tetrahydrofuran (12 mL), and the transfer quantitated with an additional portion of tetrahydrofuran (3 mL). The reaction was stirred at −78° C. for 75 minutes, 0° C. for 15 minutes, and 23° C. for 5 minutes, and then cooled to 0° C. Iodobutane (1.39 mL, 12.25 mmol, 3.5 equiv) was added, and the reaction was stirred at 0° for 1 h 30 minutes, then quenched with saturated ammonium chloride. The amide was extracted from saturated ammonium chloride (350 mL) with ethyl acetate (3×80 mL), and the oily residue was chromatographed on silica gel with 40% ethyl acetate/hexanes to afford the butylated hydrocinnamide as a yellow oil (1.03 g, 83% yield). GC analysis of the TMS ether indicated a diasteomeric purity of the amide of 98% de: 1H NMR (300 MHz, C6D6) δ7.0–7.4 (m, 10H), 5.2 (br, 1H), 4.49 (t, 1H, J=6.9 Hz), 4.02 (m, 1H), 3.90 (br, 1H), 3.78 (m, 1H), 3.03 (m, 2H), 2.70 (s, 3H), 2.57 (m, 2H), 2.02 (s, H), 0.93–1.9 (m), 0.92 (d, 3H, J=7.0 Hz), 0.84 (t, 3H, J =7.2 Hz), 0.16 (d, 3H, J=6.7 Hz); 13C NMR (75.5 MHz, CDCl3) δ177.7, 176.7, 142.2, 141.1, 140.2, 139.8, 128.9, 128.6, 128.4, 128.3, 128.2, 128.2, 127.4, 126.8, 126.3, 126.3, 126.1, 75.8, 75.3, 60.0, 58.2, 44.9, 44.2, 39.8, 39.5, 33.6, 33.1, 29.9, 29.5, 22.9, 22.8, 14.4, 14.3, 14.0, 13.9; FTIR (neat film) cm-1 3404 (s), 1624 (m).

EXAMPLE 13

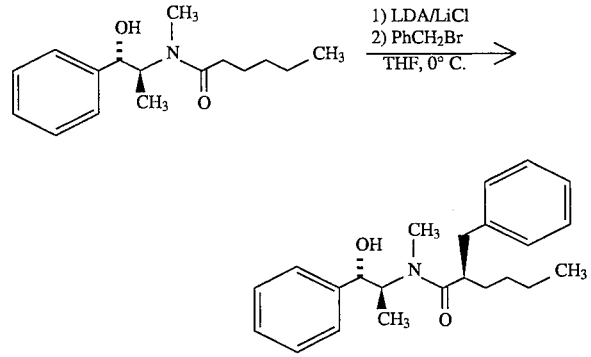

[1S-[1R*(S*),2R*]]-α-butyl-N-(2-hydroxy-1-
methyl-2-phenylethyl)-N-methyl
benzenepropionamide A dry 3-necked 2 L round-bottomed flask equipped with a mechanical stirrer was charged with lithium chloride (19.32 g, 455.58 mmol, 6.0 equiv), diisopropylamine (23.94 mL, 170.84 mmol, 2.25 equiv), and tetrahydrofuran (200 mL). The suspension was cooled to −78° C., and n-butyllithium (2.43M in hexanes, 64.99 mL, 157.93 mmol, 2.08 equiv) was added, and the mixture was warmed briefly to 0° C., then recooled to −78° C. [S-[R*,R*]]-N-(2-hydroxy-1-methyl-2-phenylethyl)-N-methyl hexanamide (20.0 g, 75.93 mmol, 1.0 equiv) was ·added at 0° C. as a solution in tetrahydrofuran (150 mL). The resulting solution was stirred at −78° C. for 50 minutes, 0° C. for 15 minutes, and 23° C. for 5 minutes, and then recooled to 0° C. Benzyl bromide (13.55 mL, 113.90 mmol, 1.5 equiv) was syringed into the reaction mixture and after 40 minutes, the reaction was quenched with saturated ammonium chloride. Most of the volatile components were removed by rotary evaporation, and the amide was extracted from saturated ammonium chloride (700 mL) with ethyl acetate (4×150 mL). The combined organic extracts were dried over sodium sulfate, and after removal of the solvent under reduced pressure, a white solid was obtained. Recrystallization from toluene (100 mL), affording the benzylated hexanamide as white crystals (23.28 g, 87% yield). GC analysis of the TMS ether indicated a diasteomeric purity of greater than 99% de: mp 120°–121° C.; 1H NMR (300 MHz, C6D6) δ7.0–7.45 (m, 10H), 4.31 (m, 1H), 4.15 (br, 1H), 3.98 (m, 1H), 3.35 (m, 1H), 2.99 (m, 1H), 2.72 (s, 3H), 2.53–2.67 (m, 2H), 2.12 (s, 3H), 1.0–2.0 (m, 6H), 0.87 (t, 3H, H7, J=7.0 Hz), 0.73–0.80 (m, H), 0.64 (d, 3H, J=6.2 Hz); 13C NMR (75.5 MHz, CDCl3) δ177.9, 176.6, 142.2, 141.0, 140.5, 139.9, 129.2, 128.9, 128.6, 128.5, 128.3, 128.2, 127.6, 126.9, 126.5, 126.3, 126.2, 76.4, 75.1, 58.2, 57.9, 44.8, 44.0, 39.6, 39.3, 32.9, 32.8, 32.1, 29.8, 29.6, 27.0, 22.8, 15.5, 14.2, 13.9; FTIR (neat film) cm-1 3369 (br, m), 2958 (m), 2929 (m), 1614 (s), 1493 (m), 1454 (m), 1412 (m), 744 (m), 700 (s).

The combined organic extracts were dried over sodium sulfate, filtered, and concentrated under reduced pressure. Purification of the residue by flash chromatography (with 35% ethyl acetate/hexanes as eluent) gave the product (308 mg, 95%) as an oil which quickly crystallized. The crude product contained an impurity resulting from cyclization to the corresponding ether (ca 5%). Analytically pure product was obtained by recrystallization from a minimum volume of ethyl acetate to give 189 mg (58%) of white crystals (1:1 mixture of rotamers) with a de of ≧90% by 1H NMR: mp 155°–156° C.; 1H NMR (300 MHz, CDCl3) δ7.26–7.38 (m, 10H), 4.83 (dd, 0.5H, J =8.8 Hz, 5.1 Hz), 4.65 (t, 0.5H, J=6.9 Hz), 4.57 (m, 1H), 4.41 (s (br), 0.5H), 4.12 (m, 0.5H), 3.70 (s(br), 0.5H), 3.46 (dd, 0.5H, J=13.7 Hz, 7.7 Hz), 3.37 (dd, 0.5H, J= 14.1 Hz, 5.7 Hz), 3.15–3.24 (m, 1H), 2.97 (s, 1.5H), 2.81 (s, 1.5H), 2.23 (d, 0.5H, J=2.7 Hz), 1.09 (d, 1.5H, J= 6.7 Hz), 1.07 (d, 1.5H, J=7.0 Hz); 13C NMR (75.5 MHz, CDCl3) δ170.0, 169.5, 141.7, 141.0, 137.4, 136.7, 129.6, 129.5, 128.8, 128.53, 128.47, 128.4, 127.8, 127.1, 126.8, 126.7, 126.4, 126.3, 76.0, 75.4, 58.1, 54.9, 54.8, 40.7, 40.3, 28.0, 15.3, 13.8; FTIR (neat film) cm-1 3388, 3029, 1633. Anal. Calcd for C19H22ClNO2 C, 68.77; H, 6.68; N, 4.22; Found C, 68.75, H,6.69, N, 4.19.

EXAMPLE 15

EXAMPLE 14

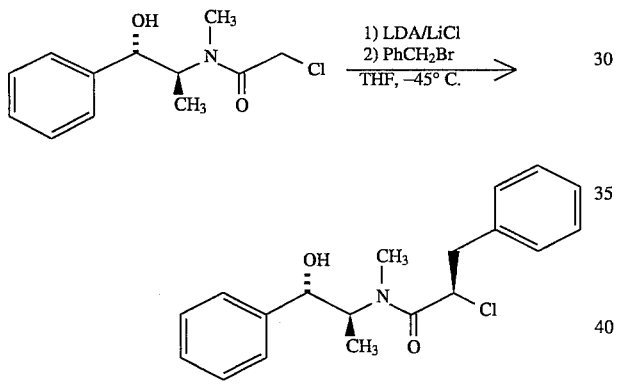

[S-(R*(S*),R*]]-α-chloro-N-(2-hydroxy-1-methyl-2-phenylethyl-N-methyl benzenepropionamide To a dry 50 mL Schlenk flask equipped with a magnetic stirrer was transferred lithium chloride (249 mg, 5.88 mmol, 6.0 equiv). The flask was evacuated, filled with argon and tetrahydrofuran (2.5 mL) was added- The solvent was vacuum degassed and diisopropylamine (0.302 mL, 2.16 mmol, 2.2 equiv) was added. The solution was cooled to −78° and a solution of n-butyllithium (1.64M in hexanes, 1.26 mL, 2.06 mmol, 2.1 equiv) was added. The reaction was warmed to 0° C., stirred for 10 minutes, and recooled to −78° C. A cold (−78° C.) solution of [S-(R*,R*)]-α-chloro-N-(2-hydroxy-1-methyl- 2-phenylethyl)-N-methyl acetamide (237 mg, 0.98 mmol, 1.0 equiv, azeotropically dried with toluene) in tetrahydrofuran (3 mL) was added via cannula, and the reaction was stirred for 1 hour at −78° C. The reaction was warmed to −45° C., stirred for 5 minutes and then benzyl bromide (0,175 mL, 1.47 mmol, 1.5 equiv) was added. The reaction was allowed to stir for 1 hr 40 minutes, and was quenched at −45° C. by addition of 0.5M potassium bisulfate. The mixture was warmed to 23° C. and the product was extracted with two portions of ethyl acetate.

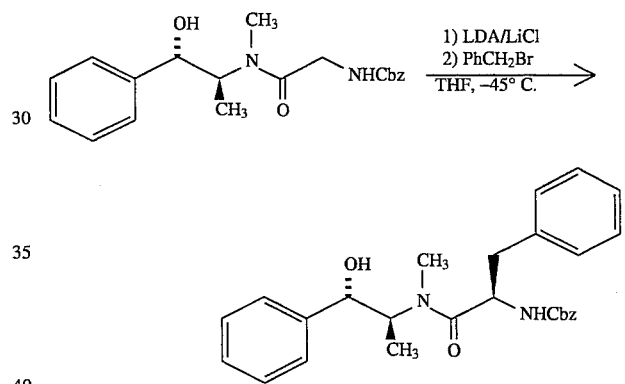

[S-(R*(S*),R*)-α-(carbobenzyloxyamino-N1-(2-hydroxy-1-methyl- 2-phenylethyl-N1-methyl benzenepropionamide To a dry 50 mL Schlenk flask equipped with a magnetic stirrer was transferred lithium chloride (0.221 g, 5.22 mmol, 10 equiv). The flask was evacuated, filled with argon and tetrahydrofuran (2.5 mL) was added. The solvent was vacuum degassed and diisopropylamine (0.234 mL, 1.67 mmol, 3.2 equiv) was added. The solution was cooled to −78° C. and a solution of n-butyllithium (1.64M in hexanes, 0.986 mL, 1.62 mmol, 3.1 equiv) was added. The reaction was warmed to 0° C., stirred for 10 minutes, and recooled to −78° C. To the reaction was added a solution of [S-(R*,R*)]-N2-(benzyloxycarbonyl)-N1-( 2-hydroxy-1-methyl-2-phenylethyl)-N1-methyl glycinamide (0.186 g, 0.522 mmol, 1.0 equiv, azeotropically dried with toluene) in tetrahydrofuran (3 mL). The reaction was warmed to 0° C. and stirred for 1 hour. The reaction was cooled to −45° C. and benzyl bromide (0.093 mL, 0.783 mmol, 1.5 equiv) was added. The reaction was stirred at −45° C. for 3 hours and was quenched by addition of 0.5M potassium bisulfate. The mixture was warmed to 23° C. and the product extracted with two portions of ethyl acetate, dried over sodium sulfate, filtered and concentrated under reduced pressure. Purification of the residue by chromatography on silica gel with ethyl acetate/ hexanes as eluent (20% to 80% gradient) gave the product (171 mg, 73%) as a foam (4:1 mixture of rotamers with a de of ≧90% (by 1HNMR), *=minor rotamer resonances), and unalkylated amide (24 mg, 13%): 1HNMR (300 MHz, CDCl3) δ7.18–7.40 (m, 15H), 5.52 (d, 1H, J=8.1 Hz), 5.65* (d, 1H, J=9.1 Hz), 4.97–5.16 (m, 2H), 4.86 (q (obs), 1H, J=7.5), 4.65 (m, 1H), 4.58, (d, 1H, J=9.1 Hz), 4.49 (d, 1H, J= 8.7 Hz), 4.26 (m, 1H), 3.44–3.83 (s (br), 1H), 3.27, (dd, 1H, J=13.7 Hz, 5.4 Hz), 2.90–3.08 (m, 2H), 2.61 (s, 3H), 0.98 (d, 3H, J=6.6 Hz), 0.79 (d, 3H, J=6.9 Hz); 13C NMR (75.5 MHZ, CDCl3) δ173.1, 172.2, 155.8, 155.6, 141.5, 141.2, 136.9, 136.3, 136.2, 136.0, 129.5, 129.3, 129.2, 128.8, 128.7, 128.6, 128.5, 128.34, 128.27, 128.12, 128.10, 128.0, 127.9, 127.81, 127.76, 126.9, 126.7, 126.6, 75.5, 75.1, 66.8, 66.5, 58.2, 56.4, 52.6, 51.8, 39.5, 38.5, 30.3, 27.1, 22.5, 15.4, 13.9; FTIR (neat film) cm-1 3402, 3303, 3030, 1714, 1633.

Method—Hydrolysis of Alkylated pseudoephedrine Amides to form Chiral Carboxylic Acids of High Enantiomeric Purity

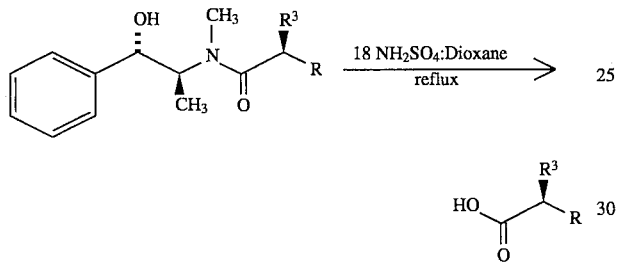

The acidic hydrolysis of the alkylated pseudoephedrine amides to the corresponding carboxylic acids with little loss of optical purity was accomplished as follows: The amide was stirred in refluxing aqueous sulfuric acid: dioxane until the reaction was complete, typically for 1–30 h. The mixture was then basified with aqueous sodium hydroxide and washed with dichloromethane to remove liberated pseudoephedrine. The resulting aqueous phase was next acidified and extracted with dichloromethane. These extracts were then dried over anhydrous sodium sulfate, filtered, and concentrated under reduced pressure to afford the pure carboxylic acid.

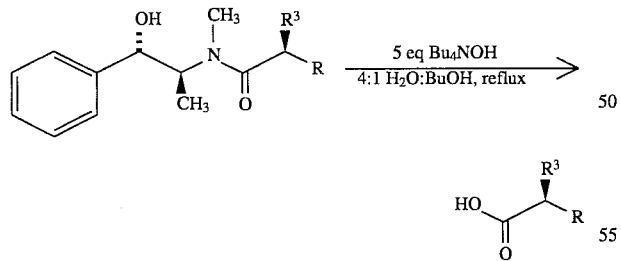

The basic hydrolysis of the alkylated pseudoephedrine amides to the corresponding carboxylic acids with little loss of optical purity was accomplished as follows: The amide was stirred with 5 equivalents tetrabutylammonium hydroxide in refluxing water: tert-butanol until the reaction was complete, typically 20–24 h. The mixture was then diluted with aqueous sodium hydroxide and washed with diethyl ether to remove liberated pseudoephedrine. The resulting aqueous phase was acidified with aqueous hydrochloric acid, saturated with sodium chloride and extracted with ethyl acetate. These extracts were washed with water, dried over anhydrous sodium sulfate, and concentrated under reduced pressure to afford the pure carboxylic acid.

EXAMPLE 16

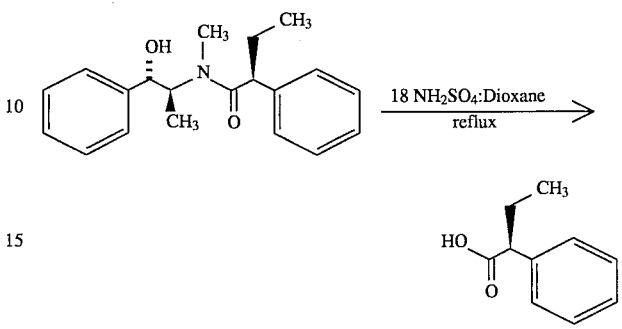

S-α-ethyl benzeneacetic acid

A 50 mL round-bottomed flask was charged with [1S[1R*(R*), 2R*]]-α-ethyl-N-(2-hydroxy-1-methyl-2-phenylethyl)-N-methyl benzeneacetamide (1.2488 g, 4.0 mmol) and 10:8 18N sulfuric acid: dioxane (18 mL) and the resulting mixture refluxed for 2 h under a Liebig condenser. The mixture was then basified with 50% aqueous sodium hydroxide, and washed with dichloromethane (2×50 mL). The remaining aqueous phase was acidified with 6N aqueous sulfuric acid and extracted with dichloromethane (3×50 mL). These extracts were dried over anhydrous sodium sulfate, filtered, and concentrated under reduced pressure to afford S-α-ethyl benzeneacetic acid (0.6306 g, 96% yield) with an enantiomeric excess of 95% (as determined by chiral GC analysis of the R-α-methylbenzyl amide of the acid).

EXAMPLE 17

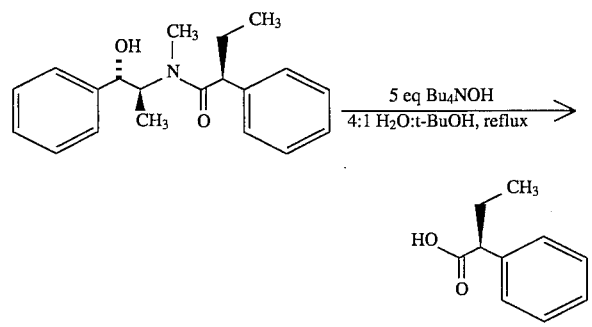

A 10 mL recovery flask equipped with a magnetic stirrer was charged with [1S-[1R*(R*), 2R*]]-α-ethyl-N-(2-hydroxy-1-methyl- 2-phenylethyl)-N-methyl benzeneacetamide (86 mg, 0.28 mmol, 1.0 equiv) and a mixture of tetrabutylammonium hydroxide (0.81g of a 40% aqueous solution, 1.25 mmol, 4.5 equiv) in 4:1 water: tert-butanol (5 mL), and the resulting mixture refluxed for 20 h under a Liebig condenser. The reaction was then poured into a separatory funnel with 1N NaOH (100 mL), and extracted with ether (3×10 mL). The aqueous phase was acidified with 3N HCl, saturated with sodium chloride, and then extracted with ethyl acetate (3× 15 mL). The ethyl acetate extracts were washed once with water (5 mL), dried over sodium sulfate, and the solvent was removed under reduced pressure to provide S-α-ethyl benzeneacetic acid (37.4 mg, 82% yield) with an enantiomeric excess of 64% (as determined by chiral GC analysis of the R-α-methylbenzyl amide of the acid).

1H NMR (300 MHz, CDCl3) δ7.25 (m, 5H), 3.41 (t, 1H, J=7.7 Hz), 2.05 (m, 1H), 1.76 (m, 1H), 0.86 (t, 3H, J=7.4 Hz); 13C NMR (75.5 MHz, CDCl3) δ180.5, 138.3, 128.6, 128.1, 127.4, 53.3, 26.3, 12.1; FTIR (neat film) cm-1 2967 (s, br, OH), 2683 (m, br), 1949 (w), 1871 (w), 1805 (w), 1712 (s, C=O), 1601 (w), 1496 (m), 1455 (s), 1415 (s), 1286 (s), 1223 (s), 1185 (m), 1082 (w), 1029 (w), 942 (m), 849 (w), 728 (s), 698 (s), 616 (w), 506 (w).

EXAMPLE 18

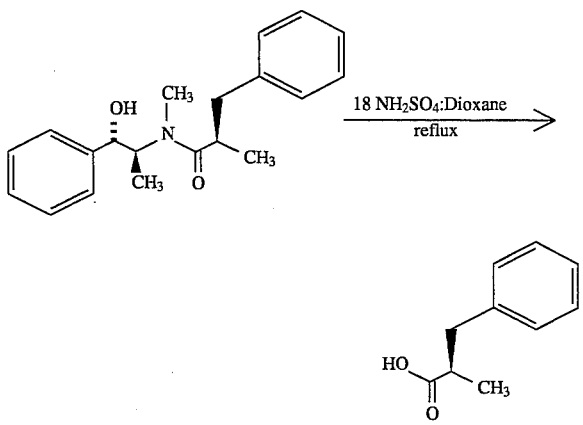

R-α-methyl benzenepropionic acid

A 50 mL round-bottomed flask was charged with [1S-[1R*(S*), 2R*]]-N-(2-hydroxy-1-methyl-2-phenylethyl)-N,2-dimethyl benzenepropion amide (1.2458g, 4.0 mmol) and 10:8 18N sulfuric acid: dioxane (18 mL). The resulting mixture was refluxed for 1 h under a Liebig condenser. The mixture was then basified with 50% aqueous sodium hydroxide, and washed with dichloromethane (2×50 mL). The remaining aqueous phase was acidified with 6N aqueous sulfuric acid and extracted with dichloromethane (3×50 mL). These extracts were dried over anhydrous sodium sulfate, filtered, and concentrated under reduced pressure to afford R-α-methyl benzenepropionic acid (0.5719 g, 87% yield) with an enantiomeric excess of 97% (as determined by chiral GC analysis of the R-α-methylbenzyl amide of the acid).

EXAMPLE 19

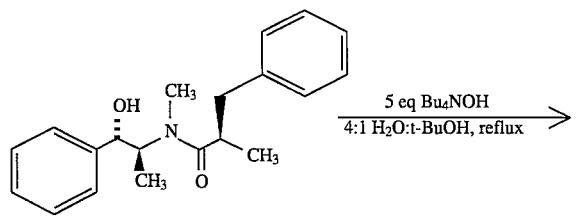

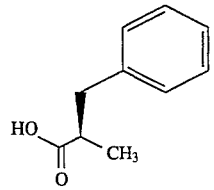

A 10 mL recovery flask equipped with a magnetic stirrer was charged with [1S-[1R*(S*), 2R*]]-N-(2-hydroxy-1-methyl-2-phenylethyl)-N,2-dimethyl benzenepropion amide (75 mg, 0.24 mmol, 1.0 equiv) and a mixture of tetrabutylammonium hydroxide (0.78g of a 40% aqueous solution, 1.21 mmol, 5 equiv) in 4:1 water: tert-butanol (5 mL), and the resulting mixture was refluxed for 22 h under a Liebig condenser. The reaction mixture was basified with 1N sodium hydroxide (100 mL), and extracted with ether (3×10 mL). The aqueous phase was acidified with 3N HCl, saturated with sodium chloride, and extracted with ethyl acetate (3×15 mL). The combined ethyl acetate extracts were washed once with water (5 mL), dried over sodium sulfate, filtered, and concentrated to give R-α-methyl benzenepropionic acid (36 mg, 91% yield) with an enantiomeric excess of 94% (as determined by chiral GC analysis of the R-α-methylbenzyl amide of the acid).

1H NMR (300 MHz, CDCl3)δ7.25 (m, 5H), 3.09 (dd, 1H, J1= 6.1 Hz, J2=13.1 Hz), 2.75 (m, 2H, H), 1.18 (d, 3H, J=6.8 Hz); 13C NMR (75.5 MHz, CDCl3)δ182.5, 139.0, 129.0, 128.4, 126.4, 41.2, 39.3, 16.5; FTIR (neat film) cm-1 2976 (s,br, OH), 2657 (m, br), 1948 (w), 1877 (w), 1806 (w), 1707 (s, C=O), 1496 (m), 1454 (s), 1417 (m), 1294 (s), 1241 (s), 1117 (w), 1082 (w), 942 (m), 744 (m), 700 (s), 549 (w).

EXAMPLE 20

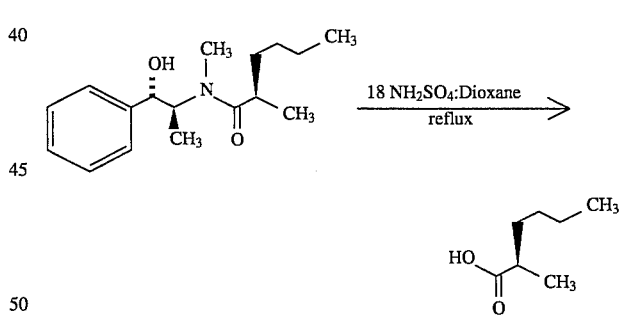

R-2-methyl hexanoic acid

A 50 mL round-bottomed flask was charged with [1S-[1R*(S*), 2R*]]-N-(2-hydroxy-1-methyl-2-phenylethyl)-N,2-dimethyl hexanamide (1.1106 g, 4.0 mmol) and 1:1 18N sulfuric acid: dioxane (16 mL). The resulting mixture refluxed for 1 h under a Liebig condenser. The mixture was then basified with 50% aqueous sodium hydroxide, and washed with dichloromethane (2×50 mL). The remaining aqueous phase was acidified with 6N aqueous sulfuric acid and extracted with dichloromethane (3×50 mL). These extracts were dried over anhydrous sodium sulfate, filtered, and concentrated under reduced pressure to afford R-2-methyl hexanoic acid (0.4728 g, 91% yield) with an enantiomeric excess of 97% (as determined by chiral GC analysis of the R-α-methylbenzyl amide of the acid).

EXAMPLE 21

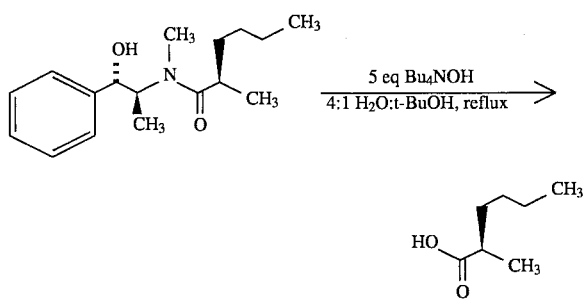

A 10 mL recovery flask equipped with a magnetic stirrer was charged with [1S-[1R*(S*), 2R*]]-N-(2-hydroxy-1-methyl- 2-phenylethyl)-N,2-dimethyl hexanamide (80 mg, 0.29 mmol, 1.0 equiv) and a mixture of tetrabutylammonium hydroxide (0.93 g of a 40% aqueous solution, 1.44 mmol, 5 equiv) in 4:1 water: tert-butanol (5 mL) and the resulting mixture refluxed for 22 h under a Liebig condenser. The reaction mixture was basified with 1N sodium hydroxide (100 mL), and extracted with ether (3×10 mL). The aqueous phase was acidified with 3N HCl, saturated with sodium chloride, and extracted with ethyl acetate (3×15 mL). The combined ethyl acetate extracts were washed once with water (5 mL), dried over sodium sulfate, filtered, and concentrated to give R-2-methyl hexanoic acid (33 mg, 88% yield) with an enantiomeric excess of 93% (as determined by chiral GC analysis of the R-e-methylbenzyl amide of the acid).

1H NMR (300 MHz, CDCl3) δ2.44 (sx, 1H, J=6.9 Hz), 1.70 (m, 1H), 1.45 (m, 1H), 1.35 (m, 4H), 1.17 (d, 3H, J=7.0 Hz),.0.90 (m, 3H); 13C NMR (75.5 MHz, CDCl3)δ183.9, 39.4, 33.2, 29.3, 22.6, 16.8, 13.9; FTIR (neat film) cm-1 3028 (s, br, OH), 2959 (s), 2657 (m), 1712 (s, C=O), 1467 (s), 1417 (m), 1380 (w), 1293 (m), 1239 (s), 1207 (m), 1154 (w), 1102 (w), 942 (m), 830 (w), 792 (w), 730 (w), 640 (w), 555 (w).

EXAMPLE 22

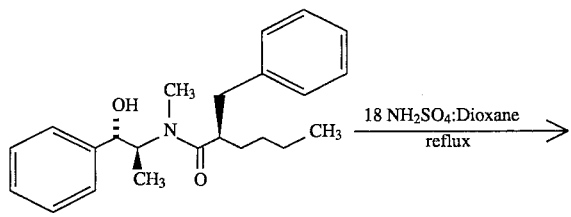

R-α-butyl benzenepropionic acid

A 50 mL round-bottomed flask was charged with [1S-[ 1R*(S*), 2R*]]-α-butyl-N-(2-hydroxy-1-methyl-2-phenylethyl)-N-methyl benzenepropionamide (1.0624 g, 3.0 mmol) and 1:1 18N sulfuric acid: dioxane (12 mL). The resulting mixture was refluxed for 22 h under a Liebig condenser. The mixture was then basified with 50% aqueous sodium hydroxide, and washed with dichloromethane (2×50 mL). The remaining aqueous phase was acidified with 6N aqueous sulfuric acid and extracted with dichloromethane (3× 50 mL). These extracts were dried over anhydrous sodium sulfate, filtered, and concentrated under reduced pressure to afford R-α-butyl benzenepropionic acid (0.5838 g, 94% yield) with an enantiomeric excess of 96% (as determined by chiral GC analysis of the R-α-methylbenzyl amide of the acid).

1H NMR (300 MHz, CDCl3) δ7.30 (m, 5H), 2.98 (dd, 1H, J1= 7.8 Hz, J2=13.5 Hz), 2.70 (m, 2H), 1.65 (m, 1H), 1.55 (m, 1H), 1.30 (m, 4H), 0.85 (m, 3H); 13C NMR (75.5 MHz, CDCl3) δ 181.8, 139.1, 128.9, 128.4, 126.4, 47.3, 38.1, 31.4, 29.3, 22.5, 13.9; FTIR (neat film) cm-1 3028 (s,br, OH), 2932 (s), 2673 (m), 1945 (w), 1873 (w), 1803 (w), 1711 (s, C=O), 1604 (w), 1496 (m), 1455 (s), 1417 (m), 1239 (s), 1240 (s), 1205 (m), 1110 (w), 1076 (w), 1030 (w), 942 (m), 832 (w), 792 (w), 743 (m), 699 (s), 556 (w).

Method—Reduction of Alkylated Pseudoephedrine Amides to form Chiral Primary Alcohols of High Enantiomeric Purity

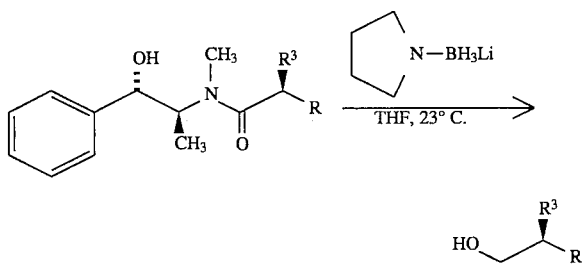

Reduction of the amide to the alcohol followed the procedure described by Singaram et al. [*Tetrahedron Lett.* 1993, 34, 1091]. The hydride was generated by reacting pyrrolidine with borane-tetrahydrofuran solution at 23° C. for 1 hour. Deprotonation with n-butyllithium at 0° C. for 30 minutes generated the active hydride species. The amide was added either neat or as a solution in tetrahydrofuran, and stirred at 23° C. for several hours. Isolation of the alcohol involved an acidic workup to remove pyrrolidine and pseudoephedrine as their hydrochloride salts, followed by flash chromatography to isolate the alcohol. In some cases it was found that yields could be improved with an additional basic workup, in order to hydrolyze residual borate esters.

EXAMPLE 23

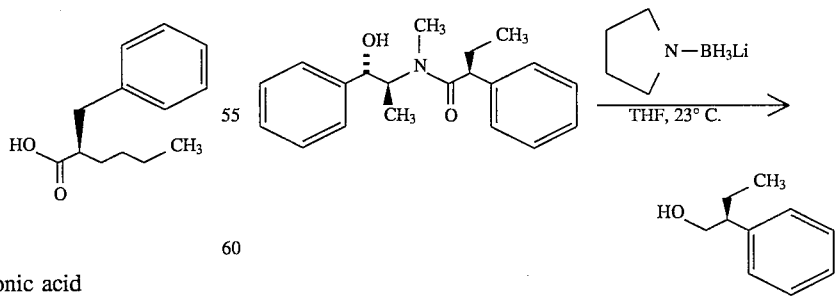

(S)-β-butyl benzenepropanol

A dry 25 mL Schlenk flask equipped with a magnetic stirrer was cooled to 0° C., and charged with pyrrolidine (0.142 mL, 1.707 mmol, 3.0 equiv) and borane.tetrahydrofuran (1.0M in tetrahydrofuran, 1.707 mL, 1.707 mmol, 3.0 equiv). The mixture was then warmed to 23° C., and stirred for 1 hour. The mixture was cooled to 0° C., and n-butyllithium (1.73M in hexanes, 0.99 mL, 1.707 mmol, 3.0 equiv) was added, and the reaction stirred for 35 minutes. [1S-[1R*(R*),2R*]]-α-butyl-N-( 2-hydroxy-1-methyl-2-phenylethyl)-N-methyl benzenepropionamide (0.201 g, 0.569 mmol, 1.0 equiv) was added as a tetrahydrofuran solution (2 mL), and the reaction was warmed to 23° C. and stirred for 3 hours and 5 minutes. The reaction was quenched with 1N HCl, and the product extracted from 1N HCl (100 mL) with ether (4×25 mL). The ether extracts were washed with 1:1 brine/1N HCl (2×10 mL), dried over sodium sulfate, and concentrated. The residue was chromatographed with 25% ethyl acetate/hexanes to afford the alcohol (96 mg, 88% yield) as a colorless oil. Analysis of the Mosher ester indicated an enantiomeric purity of 98% ee: 1H NMR (300 MHz, C6D6) δ7.0–7.3 (m, 5H), 3.25 (d, 2H, J=5.1 Hz), 2.59 (dd, 1H, J=13.5 Hz, 7.6 Hz), 2.48 (dd, 1H, J=13.5 Hz, 6.5 Hz), 1.60 (m, 1H), 1.31 (m, 1H), 1.20 (m, 4H), 0.84 (m, 3H); 13C NMR (75.5 MHz, CDCl3) δ140.8, 129.1, 128.1, 125.7, 64.6, 42.4, 37.5, 30.3, 29.0, 22.9, 14.0. FTIR (neat film) cm-1 3342 (br, m), 3026 (w), 2955 (s), 2928 (m), 1495 (m), 1454 (m), 1050 (m), 1030 (m), 742 (m), 700 (m).

EXAMPLE 24

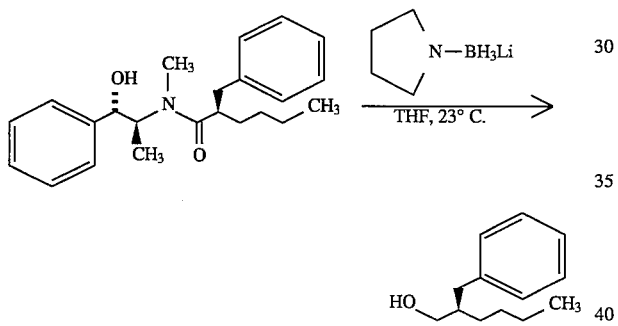

(R)-β-butyl benzenepropanol

A dry 25 mL Schlenk flask equipped with a magnetic stirrer was cooled to 0° C. and charged with pyrrolidine (0.104 mL, 1.242 mmol, 3.0 equiv) and borane.tetrahydrofuran (1.0M in tetrahydrofuran, 1.242 mL, 1.242 mmol, 3.0 equiv). The mixture was warmed to 23° C. for 1 hour, then recooled to 0° C. n-Butyllithium (1.73M in hexanes, 0.72 mL, 1.242 mmol, 3.0 equiv) was added, and the reaction was stirred at 0° C. for 30 minutes. [1S-[1R*(S*),2R*]]-α-butyl-N-(2-hydroxy- 1-methyl-2-phenylethyl)-N-methyl benzenepropionamide (0.146 g, 0.414 mmol, 1.0 equiv) was added as a solution in tetrahydrofuran (2 mL), and stirred at 23° C. for 5 hours. The reaction was quenched with aqueous hydrochloric acid. The product was extracted from 1N HCl (100 mL) with ether (4× 25 mL), and the ether extracts washed with 1:1 brine/1N HCl (2×10 mL). The ether extracts were dried over sodium sulfate, concentrated, and the residue was chromatographed with 25% ethyl acetate/ hexanes to afford the alcohol (70 mg, 88% yield) as a colorless oil. Analysis of the Mosher ester indicated an enantiomeric purity of approximately 99% ee: 1H NMR (300 MHz, C6D6) δ7.0–7.3 (m, 5H), 3.25 (d, 2H, J=5.1 Hz), 2.59 (dd, 1H, J=13.5 Hz, 7.6 Hz), 2.48 (dd, 1H, J= 13.5 Hz, 6.5 Hz), 1.60 (m, 1H), 1.31 (m, 1H), 1.20 (m, 4H), 0.84 (m, 3H); 13C NMR (75.5 MHz, CDCl3) δ140.8, 129.1, 128.1, 125.7, 64.6, 42.4, 37.5, 30.3, 29.0, 22.9, 14.0; FTIR (neat film) cm-1 3342 (br, m), 2955 (s), 2928 (m), 1495 (m), 1454 (m), 1050 (m), 1030 (m), 742 (m), 700 (m).

EXAMPLE 25

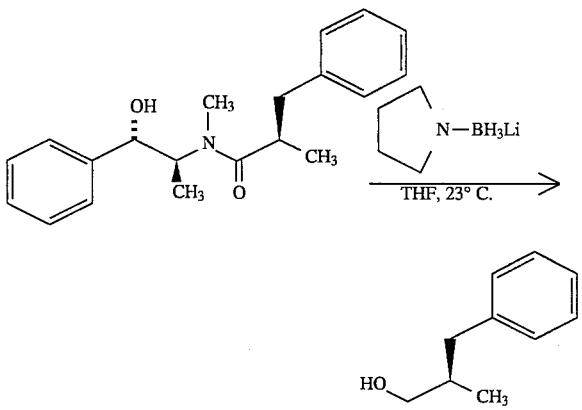

(R)-β-methyl benzenepropanol

A dry 100 mL Schlenk flask equipped with a magnetic stirrer was cooled to 0° C. and charged with pyrrolidine (0.80 mL, 9.63 mmol, 3.0 equiv) and borane.tetrahydrofuran (1.0M in tetrahydrofuran, 9.63 mL, 9.63 mmol, 3.0 equiv). The mixture was warmed to 23° C., and stirred for 1 hour. It was recooled to 0° C., and n-butyllithium (1.71M in hexanes, 5.63 mL, 9.63 mmol, 3.0 equiv) was added, and the reaction was stirred at 0° C. for 30 minutes. [1S-[1R*(S*), 2R*]]-N-(2-hydroxy- 1-methyl-2-phenylethyl)-N,2-dimethyl benzenepropionamide (1.0 g, 3.21 mmol, 1.0 equiv) was added via cannula as a solution in tetrahydrofuran (9 mL), and the transfer quantitated with an additional portion of tetrahydrofuran (1 mL), and the mixture stirred at 23° C. for 6 hours. The reaction was quenched with aqueous hydrochloric acid, and the product was extracted from 1N HCl (350 mL) with ether (4×50 mL). The ether extracts were washed with 1:1 brine/1N HCl (2×25 mL), concentrated, and poured into 1N sodium hydroxide (100 mL) and stirred at 23° C. for 30 minutes. The mixture was extracted with ether (3×30 mL), and the ether extracts were washed with 1:1 brine/1N NaOH (2×10 mL), dried over sodium sulfate, and concentrated. Flash column chromatography (35% ether/petroleum ether) afforded the desired alcohol (405 mg, 84% yield) as a colorless oil. Analysis of the Mosher ester indicated an enantiomeric purity of approximately 99% ee: 1H NMR (300 MHz, C6D6) δ 7.0–7.2 (m, 5H), 3.15 (m, 2H), 2.62 (dd, 1H, J=13.3 Hz, 6.2 Hz), 2.22 (dd, 1H, J=13.3 Hz, 8.0 Hz), 1.70 (m, 1H), 0.77 (d, 3H, J=6.7 Hz), 0.62 (t, 1H, J=5.2 Hz). 13C NMR (75.5 MHz, CDCl3) δ140.6, 129.0, 128.2, 125.7, 67.4, 39.6, 37.7, 16.4; FTIR (neat film) cm-1 3332 (s), 3001 (m), 2956 (s), 2922 (s), 2872 (s) 1603 (m), 1495 (s), 1454 (s), 1378 (m), 1032 (s), 986 (m), 739 (s), 700 (s).

EXAMPLE 26

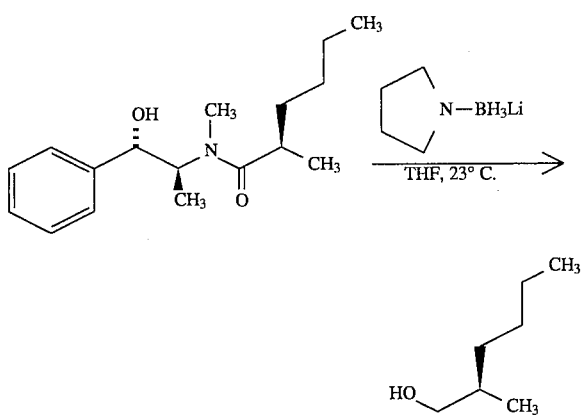

(R)-2-methyl-1-hexanol

A dry 200 mL Schlenk flask equipped with a magnetic stirrer was cooled to 0° C. and charged with pyrrolidine (1.81 mL, 21.63 mmol, 3.0 equiv) and borane.tetrahydrofuran (1.0M in tetrahydrofuran, 21.63 mL, 21.63 mmol, 3.0 equiv). The mixture was warmed to 23° C. and stirred for 1 hour. It was recooled to 0° C., and n-butyllithium (1.71M in hexanes, 12.65 mL, 21.63 mmol, 3.0 equiv) was added, and the reaction was stirred at 0° C. for 30 minutes. The ice bath was removed, and [1S-[1R*(S*), 2R*]]-N-(2-hydroxy-1-methyl-2-phenylethyl)-N, 2-dimethyl hexanamide (2.0 g, 7.21 mmol, 1.0 equiv) was added neat, and stirred at 23° C. overnight. The reaction was quenched with aqueous hydrochloric acid, diluted with 1N HCl (300 mL), and extracted with ether (4× 60 mL). The ether extracts were washed with 1:1 brine/1N HCl (2×15 mL), and then concentrated. The residue was stirred in 1N NaOH (100 mL) for 30 minutes at 23° C., and extracted with ether (4×25 mL). These ether extracts were washed with 1:1 brine/1N NaOH (2×20 mL), dried over sodium sulfate, and concentrated. Flash chromatography (40% ether/petroleum ether) of the residue afforded the desired alcohol (600 mg, 72% yield). Analysis of the Mosher ester indicated an enantiomeric purity of approximately 98% ee: 1H NMR (300 MHz, C6D6) δ3.12–3.26 (m, 2H), 0.92–1.44 (m, 7H), 0.87 (t, 3H, J=6.9 Hz), 0.83 (d, 3H, J=6.6 Hz), 0.69 (s, 1 H); 13C NMR (75.5 MHz, CDCl3) δ68.0, 36.0, 33.2, 29.6, 23.4, 16.8, 14.3; FTIR (neat film) cm-1 3339 (br, s), 2956 (s), 2928 (s), 2873 (s), 1468 (m), 1379 (m), 1039 (m).

EXAMPLE 27

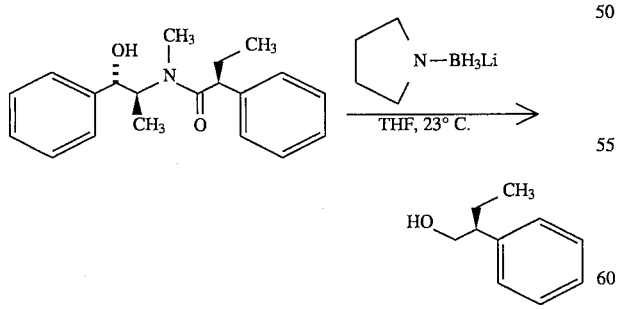

(S)-β-ethyl benzeneethanol

A dry 200 mL Schlenk flask equipped with a magnetic stirrer was cooled to 0° C. and charged with pyrrolidine (1.61 mL, 19.27 mmol, 3.0 equiv) and borane.tetrahydrofuran (1.0M in tetrahydrofuran, 19.27 mL, 19.27 mmol, 3.0 equiv). The mixture was warmed to 23° C. and stirred for 1 hour, before being recooled to 0° C. n-Butyllithium (1.71M in hexanes, 11.27 mL, 19.27 mmol, 3.0 equiv) was added, and the reaction was stirred at 0° C. for 30 minutes. The ice bath was removed, and [1S-[1R*(R*), 2R*]]-α-ethyl-N-(2-hydroxy-1-methyl- 2-phenylethyl)-N-methyl benzeneacetamide (1.99 g, 7.21 mmol, 1.0 equiv) was added neat, and the reaction was stirred at 23° C. overnight. The reaction was quenched with aqueous hydrochloric acid, diluted with 1N HCl (300 mL), and extracted with ether (4×60 mL). The ether extracts were washed with 1:1 brine/1N HCl (2×15 mL), and then concentrated. The residue was stirred in 1N NaOH (100 mL) for 30 minutes at 23° C., and extracted with ether (4×25 mL). These ether extracts were washed with 1:1 brine/1N NaOH (2×20 mL),, dried over sodium sulfate, and concentrated. Flash chromatography (40% ether/petroleum ether) of the residue afforded the desired alcohol (819 mg, 85% yield) as a colorless oil: 1H NMR (300 MHz, C6D6) δ7.0–7.2 (m, 5H), 3.48 (m, 2H), 2.44 (m, 1H), 1.58–1.65 (m, 1H), 1.36–1.45 (m, 1H), 0.91 (t, 1H, J=5.3 Hz), 0.72 (t, 3H, J=7.4 Hz); 13C NMR (75.5 MHz, CDCl3) δ: 142.2, 128.6, 128.1, 126.6, 67.3, 50.4, 24.9, 11.9; FTIR (neat film) cm-1: 3354 (br, s), 3028 (m), 2961 (s), 2930 (s), 2874 (s), 1602 (w), 1494 (s), 1454 (s), 1379 (m), 1038 (S), 760 (S), 700 (S).

Method—Reduction of Alkylated Pseudoephedrine Amides to form Chiral Aldehydes of High Enantiomeric Purity

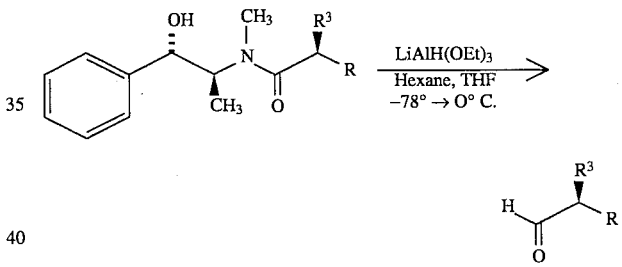

Reduction of the amide to the aldehyde followed the procedure described by Brown et al. [*J. Am. Chem. Soc.* 1964, 86, 1089]. The hydride was generated by the addition of ethyl acetate to lithium aluminum hydride in either tetrahydrofuran, hexanes, pentane, or toluene at 0 ° C. over a period of 1–2 hours. Reaction of the hydride with pseudoephedrine amides took place at 0° C. in approximately 1 hour. The reaction was quenched by transfer into an aqueous mixture of 1N hydrochloric acid and trifluoroacetic acid. The acidic workup was necessary for increased yields. The aldehyde was then isolated following extractive workup and flash chromatography.

EXAMPLE 28

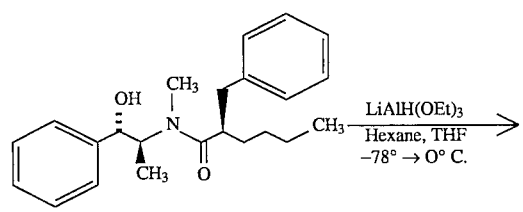

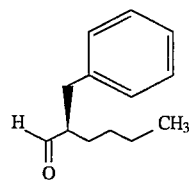

(R)-α-butyl benzenepropanal

A dry 100 mL Schlenk flask equipped with a magnetic stirrer was charged with lithium aluminum hydride (0.259 g, 6.48 mmol, 2.3 equiv) in a nitrogen-filled drybox. The hydride was suspended in hexanes (12 mL), and cooled to 0° C. Ethyl acetate (0.931 mL, 9.53 mmol, 3.38 equiv) was added by syringe pump over a 1.5 hour interval. Upon completion of addition, the hydride suspension was cooled to −78° C. and [1S-[1R*(S*),2R*]]-α-butyl-N-(2-hydroxy-1-methyl-2-phenylethyl)-N-methyl benzene propionamide (0.996 g, 2.82 mmol, 1.0 equiv) was added as a solution in tetrahydrofuran (8 mL). The reaction was warmed to 0° C., and stirred for 45 minutes. The reaction was quenched by cannula transfer into a 0° C. mixture of trifluoroacetic acid (2.17 mL, 28 mmol, 10 equiv) and 1N HCl (15 mL), and the mixture stirred for 5 minutes. The mixture was poured into 1N HCl (150 mL), the layers were partitioned, and the aqueous phase was extracted with ethyl acetate (3×25 mL). The combined organic extracts were basified with saturated sodium bicarbonate (35 mL), and the flocculent emulsion was filtered through a plug of celite loaded onto a coarse frit. The aqueous layer was removed, and the organic fraction was dried over sodium sulfate, filtered, and concentrated. Flash chromatography (9% ethyl acetate/hexanes) afforded the aldehyde (0.439 g, 82% yield) as a colorless oil. GC Analysis of the amide derived from coupling (R)-(+)-α-methylbenzylamine with the carboxylic acid (derived from sodium chlorite oxidation of the aldehyde) indicated an enantiomeric purity greater than 97% ee: 1H NMR (300 MHz, C6D6) δ9.34 (d, 1H, J=2.3 Hz), 6.9–7.3 (m, 5H), 2.71 (dd, 1H, J=13.9 Hz, 7.2 Hz), 2.36 (dd, 1H, J=13.9 Hz, 7.0 Hz), 2.22 (m, 1H), 1.31 (m, 1H), 0.9–1.2 (m, 5H), 0.74 (m, 3H); 13C NMR (75.5 MHz, CDCl3) δ 204.7, 138.9, 128.9, 128.5, 126.3, 53.4, 35.0, 29.0, 28.3, 22.7, 13.8; FTIR (neat film) cm-1: 3027 (w), 2957 (m), 2930 (m) 2859 (m), 2713 (w), 1726 (s), 1496 (m), 1454 (m), 745 (m), 700 (m).

EXAMPLE 29

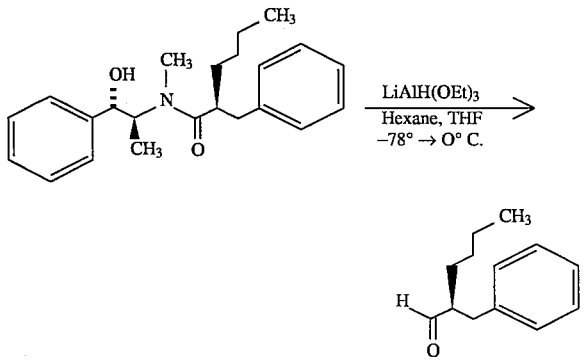

(S)-α-butyl benzenepropanal

A dry 100 mL Schlenk flask equipped with a magnetic stirrer was charged with lithium aluminum hydride (0.361 g, 9.513 mmol, 2.3 equiv) in a nitrogen-filled drybox. The hydride was suspended in hexanes (18 mL) and cooled to 0° C. Ethyl acetate (1.35 mL, 13.78 mmol, 3.33 equiv) was added over a 1.5 hour period, then the hydride suspension was cooled to −78° C. [1S-[1R*(R*),2R*]]-α-butyl-N-(2-hydroxy-1-methyl-2-phenylethyl)-N-methyl benzenepropionamide (1.46 g, 4.13 mmol, 1.0 equiv) was added in as a solution in tetrahydrofuran (10 mL), and the reaction was warmed to 0° C. The reaction was stirred for one hour, and quenched with 1N HCl. Following aqueous workup, flash column chromatography (8% ethyl acetate/hexanes) afforded the desired aldehyde (669 mg, 85% yield) as a colorless oil: 1H NMR (300 MHz, C6D6) δ9.34 (d, 1H, J=2.3 Hz), 6.9–7.3 (m, 5H), 2.71 (dd, 1H, J=13.9 Hz, 7.2 Hz), 2.36 (dd, 1H, J=13.9 Hz, 7.0 Hz), 2.22 (m, 1H), 1.31 (m, 1H), 0.9–1.2 (m, 5H), 0.74 (m, 3H); 13C NMR (75.5 MHz, CDCl3) δ204.7, 138.9, 128.9, 128.5, 126.3, 53.4, 35.0, 29.0, 28.3, 22.7, 13.8; FTIR (neat film) cm-1 3027 (w), 2957 (m), 2930 (m) 2859 (m), 2713 (w), 1726 (s), 1496 (m), 1454 (m), 745 (m), 700 (m).

EXAMPLE 30

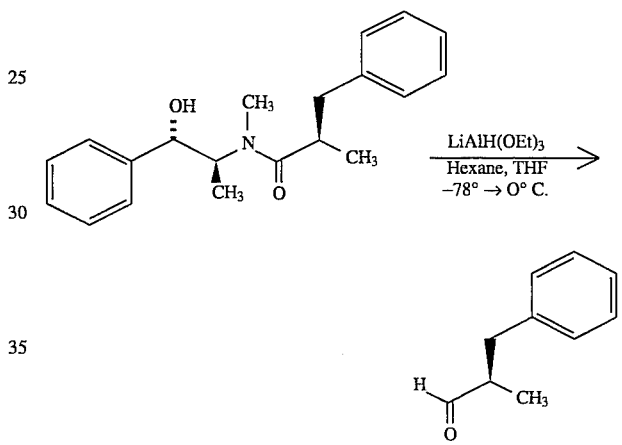

(R)-α-methyl benzenepropanal

A dry 100 mL Schlenk flask equipped with a magnetic stirrer was charged with lithium aluminum hydride (0.444 g, 11.11 mmol, 2.3 equiv) in a nitrogen-filled drybox. The hydride was suspended in hexanes (26 mL) and cooled to 0° C. Ethyl acetate (1.59 mL, 16.34 mmol, 3.38 equiv) was added by syringe pump over a 1.5 hour period, then the hydride suspension was cooled to −78° C. [1S-[1R*(S*), 2R*]]-N-(2-hydroxy- 1-methyl-2-phenylethyl)-N,2-dimethyl benzenepropionamide (1.505 g, 4.83 mmol, 1.0 equiv) was added as a solution in tetrahydrofuran (17 mL), and the reaction warmed to 0° C. The reaction was stirred for 30 minutes, and quenched by cannula transfer into a 23° C. solution of 1N HCl (60 mL) and trifluoroacetic acid (3.7 mL, 48 mmol, 10 equiv). This solution was stirred for 5 minutes, diluted with 1N HCl (100 mL), and the layers were separated. The aqueous layer was extracted with ethyl acetate (3×20 mL), and the combined organic extracts were basified with saturated sodium bicarbonate (35 mL). The flocculent emulsion was filtered through celite loaded onto a coarse frit, and the aqueous layer was removed. The aqueous layer was extracted once with ethyl acetate (10 mL), and the combined organic extracts were dried over sodium sulfate, filtered, and concentrated. Flash chromatography (10% ethyl acetate/hexanes) afforded the aldehyde (0.551 g, 77% yield) as a colorless oil. Analysis of the derived Mosher ester indicated an enantiomeric purity of 93% ee: 1H NMR (300 MHz, C6D6) δ9.29 (d, 1H, J=1.2 Hz), 6.8–7.12 (m, 5H), 2.72 (dd, 1H, J=13.2 Hz, 5.4 Hz), 2.0–2.2 (m, 2H), 0.69 (d, 3H, J=6.9 Hz); 13C NMR (75.5 MHz, CDCl3) δ 204.3, 138.7, 128.9, 128.4, 126.3, 48.0, 36.5, 13.1. FTIR (neat film) cm-1 3028 (m), 2971 (m), 1932 (m), 2814 (w), 2716 (w), 1723 (s), 1496 (m), 1454 (m), 742 (m), 701 (s).

EXAMPLE 31

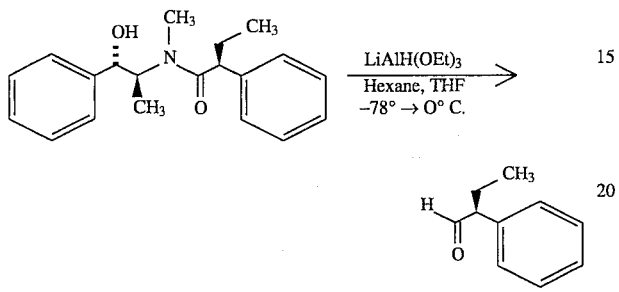

(S)-α-ethyl benzeneacetaldehyde

A dry 100 mL Schlenk flask equipped with a magnetic stirrer was charged with lithium aluminum hydride (0.441 g, 11.04 mmol, 2.3 equiv) in a nitrogen-filled drybox. The hydride was suspended in hexanes (21 mL) and cooled to 0° C. Ethyl acetate (1.59 mL, 16.23 mmol, 3.38 equiv) was added over a 1.5 hour period, then the hydride suspension was cooled to −78° C. [1S-[1R*(R*),2R*]]-α-ethyl-N-(2-hydroxy-1-methyl- 2-phenylethyl)-N-methyl benzeneacetamide (1.495 g, 4.80 mmol, 1.0 equiv) was added in as a solution in tetrahydrofuran (14 mL), and the reaction was warmed to 0° C. The reaction was stirred for 55 minutes, and quenched by cannula transfer into a 23° C. solution of 1N HCl (60 mL) and trifluoroacetic acid (3.7 mL, 48 mmol, 10 equiv). The mixture was stirred at 23° C. for 5 minutes, diluted with 1N HCl (100 mL), and the layers separated. The aqueous layer was extracted with ethyl acetate (3×20 mL), and the combined organic extracts were basified with saturated sodium bicarbonate (35 mL), and the flocculent emulsion was filtered through celite loaded onto a coarse frit. The aqueous layer was removed, and the organic layer dried over sodium sulfate, filtered, and concentrated. Flash chromatography (10% ethyl acetate/hexanes) afforded the desired aldehyde (0.569 g, 80% yield) as a colorless oil. GC analysis of the amide derived by coupling the acid (from oxidation of the aldehyde with sodium chlorite) with (R)-(+) x-methylbenzylamine indicated an enantiomeric purity of the aldehyde of 90% ee: 1H NMR (300 MHz, C6D6) δ9.34 (d, 1H, J =1.8 Hz), 6.8–7.15 (m, 5H), 2.87 (m, 1H), 1.82–1.91 (m, 1H), 1.43–1.53 (m, 1H), 0.66 (d, 3H, J=7.4 Hz); 13C NMR (75.5 MHz, CDCl3) δ200.9, 136.2, 128.9, 128.7, 127.4, 60.7, 22.8, 11.6; FTIR (neat film) cm-1 2966 (m), 2934 (m), 2876 (m), 1727 (s), 1493 (m), 1454 (m), 701 (m).

EXAMPLE 32

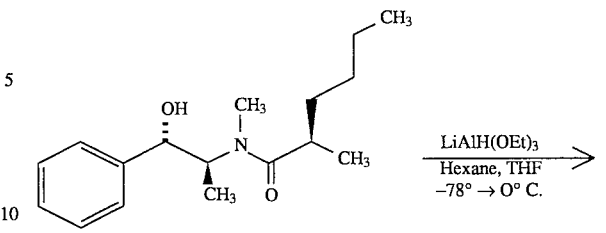

(R)-2-methylhexanal

A dry 100 mL Schlenk flask equipped with a magnetic stirrer was charged with lithium aluminum hydride (0.328 g, 8.211 mmol, 2.3 equiv) in a nitrogen-filled drybox. The hydride was suspended in hexanes (16 mL) and cooled to 0° C. Ethyl acetate (1.17 mL, 12.07 mmol, 3.38 equiv) was added over a 1.5 hour period, then the hydride suspension was cooled to −78° C. [1S-[1R*(S*), 2R*]]-N-(2-hydroxy-1-methyl- 2-phenylethyl)-N,2-dimethyl hexanamide (0.99 g, 3.57 mmol, 1.0 equiv) was added as a solution in tetrahydrofuran (9 mL), and the reaction was warmed to 0° C. The reaction was stirred for 65 minutes, and quenched by cannula transfer into a 23° C. solution of 1N HCl (45 mL) and trifluoroacetic acid (2.75 mL, 36 mmol, 10 equiv). The mixture was stirred at 23° C. for 5 minutes, diluted with 1N HCl (100 mL), and the layers separated. The aqueous layer was extracted with ethyl acetate (3×20 mL), and the combined organic extracts were basified with saturated sodium bicarbonate (30 mL), and the flocculent emulsion was filtered through celite loaded onto a coarse frit. GC analysis, using the (R)-(+)-α-methylbenzyl amide of (R)-2-methylhexanoic acid as an internal standard, indicated a yield of 78±3%. Oxidation of the aldehyde to the carboxylic acid with sodium chlorite, followed by coupling with the (R)-(+)-α-methylbenzylamine and subsequent GC analysis indicated an enantiomeric purity of the 2-methylhexanal of greater than 98% ee: 1H NMR (300 MHz, C6D6) δ9.27 (d, 1H, J=1.8 Hz), 1.74–1.92 (m, 1H), 0.85–1.15 (m, 6H), 0.78 (t, 3H, J=7.0 Hz), 0.75 (d, 3H, J =7.0 Hz). FTIR (neat film) cm-1 2959 (s), 2926 (s), 2872 (m), 1729 (m), 1455 (m), 1229 (m), 1041 (m).

Method—Addition of Alkyllithium Reagents to Pseudoephedrine Amides to form Chiral Ketones of High Enantiomeric Purity

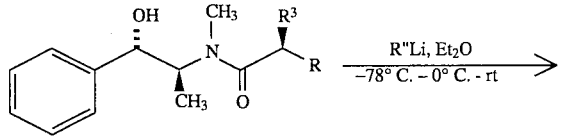

-continued

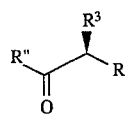

The preparation of ketones of high optical purity from the pseudoephedrine amides was achieved as follows: Two to four equivalents of an alkyllithium or aryllithium reagent were added to a −78° C.≈0.1M mixture of the pseudoephedrine amide in diethyl ether. The mixture was briefly warmed to 0° C. and then to 23° C. before being cooled again to −78° C. and quenched by addition of diisopropylamine followed by 10% glacial acetic acid/diethyl ether. This mixture was then diluted with ethyl acetate, washed with saturated sodium bicarbonate and water, and concentrated under reduced pressure. This crude concentrate was purified by flash chromatography through silica affording the desired ketone in ca. 90% yield.

EXAMPLE 33

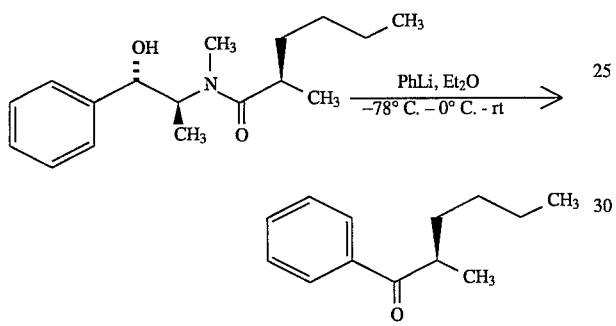

R-2-methyl-1-phenyl-1-hexanone

To a flame-dried 100 mL round-bottomed flask equipped with magnetic stir bar was added [1S-[1R*(S*), 2R*]]-N-(2-hydroxy- 1-methyl-2-phenylethyl)-N,2-dimethyl hexanamide (1.0040 g, 3.6 mmol, 1.0 equiv.). The amide was azeotropically dried under reduced pressure as a solution with toluene (10 mL) and the reaction flask flushed with dry argon. Diethyl ether (36 mL) was added to the residue and the resulting solution cooled to −78° C. Phenyllithium (4.5 mL, 1.94M, 8.7 mmol, 2.4 equiv.) was added via syringe and the mixture warmed initially to 0° C. (10 min) and then to 23° C. TLC (50% ethyl acetate/hexanes) analysis of the mixture at this point showed no starting material. The mixture was cooled again to 0° C. and diisopropylamine (0.51 mL, 3.6 mmol, 1.0 equiv.) was added to the mixture, followed 15 min later by 10% acetic acid/diethyl ether (10 mL). The mixture was extracted with water (50 mL) and the aqueous phase back extracted with ethyl acetate (50 mL) and dichloromethane (2×50 mL). The combined organic phases were dried over anhydrous sodium sulfate, decanted, and concentrated under reduced pressure. Flash chromatography (3–5% ethyl acetate/hexanes) of this concentrate then afforded R-2-methyl-1-phenyl-1-hexanone (0.6361 g, 92% yield) as a slightly yellow oil, with an ee of 92% (as determined by NMR analysis of the Mosher ester derived from the alcohol obtained from reduction of the ketone): 1H NMR (300 MHz, CDCl3) δ7.95 (m, 2H), 7.50 (m, 3H), 3.46 (sx, 1H, J=6.8 Hz), 1.80 (m, 1H), 1.45 (m, 1H), 1.30 (m, 4H), 1.19 (d, 3H, J=6.9 Hz), 0.87 (m, 3H); 13C NMR (75.5 MHz, CDCl3) δ204.5, 136.7, 132.7, 128.6, 128.2, 40.5, 33.4, 29.6, 22.8, 17.2, 13.9; FTIR (neat film) cm-1 3063 (w), 2959 (s), 2859 (s), 1964 (w), 1905 (w), 1817 (w), 1774 (w), 1682 (s,), 1596 (m), 1579 (m), 1448 (s), 1376 (m), 1230 (s), 1204 (s), 970 (s), 793 (w), 704 (s), 654 (w).

EXAMPLE 34

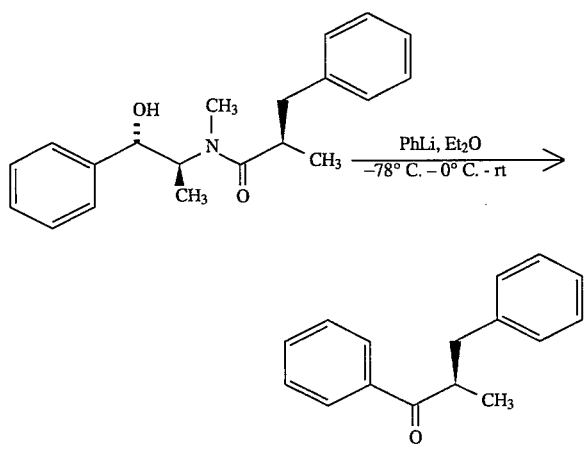

R-2-methyl-1,3-diphenyl-1-propanone

To a flame-dried 100 mL round-bottomed flask equipped with magnetic stir bar was added [1S-[1R*(S*),2R*]]-N-(2-hydroxy- 1-methyl-2-phenylethyl)-N,2-dimethyl benzenepropionamide (1.0143 g, 3.3 mmol, 1.0 equiv.). The amide was azeotropically dried under reduced pressure as a solution with toluene (12 mL) and the reaction flask flushed with dry argon. Diethyl ether (33 mL) was added to the residue and the resulting slurry cooled to −78° C. Phenyllithium (4.1 mL, 1.94M, 7.9 mmol, 2.4 equiv.) was added via syringe and the mixture warmed initially to 0° C. (15 min) and then to 23° C. TLC (50% ethyl acetate/hexanes) analysis of the mixture at this point showed no starting material. The mixture was cooled again to 0° C. and diisopropylamine (0.46 mL, 3.3 mmol, 1.0 equiv.) was added to the mixture, followed 15 min later by 10% acetic acid/diethyl ether (10 mL). The mixture was extracted with water (50 mL) and the aqueous phase back extracted with ethyl acetate (50 mL) and dichloromethane (2 x 50 mL). The combined organic phases were dried over anhydrous sodium sulfate, decanted, and concentrated under reduced pressure. Flash chromatography (3–10% ethyl acetate/hexanes) of this concentrate then afforded R-2-methyl-1,3-diphenyl-1-propanone (0.6544 g, 90% yield) as a slightly yellow oil with an ee of 92% (as determined by NMR analysis of the Mosher ester derived from the alcohol obtained from reduction of the ketone): 1H NMR (300 MHz, CDCl3) δ7.1– 7.8 (m, 10H), 3.79 (sx, 1H, J=6.9 Hz), 3.22 (dd, 1H, J1= 6.3 Hz, J2=13.7 Hz), 2.74 (dd, 1H, J1=7.9 Hz, J2=13.7) 1.25 (d, 3H, J=6.9 Hz); 13C NMR (75.5 MHz, CDCl3) δ 203.7, 139.9,136.4, 132.9, 129.1, 128.6, 128.3, 128.2, 126.2, 42.7, 39.3, 17.4; FTIR (neat film) cm-1 3062 (m), 3026 (m), 2969 (m), 1679 (s), 1596 (m), 1578 (m), 1495 (s), 1449 (s), 1374 (m), 1281 (m), 1230 (s), 1193 (m), 973 (s), 740 (m), 699 (s).

EXAMPLE 35

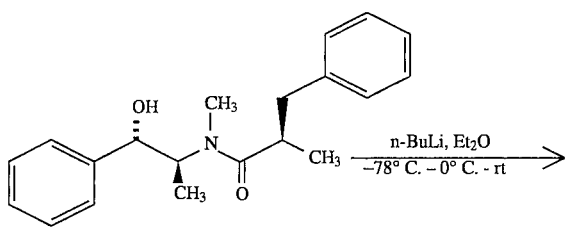

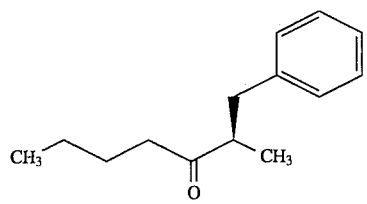

R-2-methyl-1-phenyl-3-heptanone

To a flame-dried 100 mL round-bottomed flask equipped with magnetic stir bar was added [1S-[1R*(S*), 2R*]]-N-(2-hydroxy- 1-methyl-2-phenylethyl)-N,2-dimethyl benzenepropionamide (1.0374 g, 3.3 mmol, 1.0 equiv.). The amide was azeotropically dried under reduced pressure as a solution with toluene (10 mL) and the reaction flask flushed with dry argon. Diethyl ether (33 mL) was added to the residue and the resulting slurry cooled to −78° C. n-Butyllithium (4.5 mL, 1.71M, 8.7 mmol, 2.3 equiv.) was added via syringe and the mixture warmed initially to 0° C. (10 min) and then to 23° C. TLC (50% ethyl acetate/hexanes) analysis of the mixture at this point showed no starting material. The mixture was cooled again to 0° C. and diisopropylamine (0.47 mL, 3.3 mmol, 1.0 equiv.) added to the mixture, followed 15 min. later by 10% acetic acid/diethyl ether (10 mL). The mixture was extracted with water (30 mL) and the aqueous phase back extracted with ethyl acetate (40 mL) and dichloromethane (2×40 mL). The combined organic phases were dried over anhydrous sodium sulfate, decanted, and concentrated under reduced pressure. Flash chromatography (5% ethyl acetate/hexanes) of this concentrate then afforded R-2-methyl-1-phenyl-3-heptanone (0.6060 g, 89% yield) as a slightly yellow oil: 1H NMR (300 MHz, CDCl3) δ7.20 (m, 5H), 2.97 (dd, 1H, J1=7.1 Hz, J2= 13.2 Hz), 2.83 (sx, 1H, J=7.0 Hz), 2.55 (dd, 1H, J1=7.3 Hz, J2 13.2 Hz), 2.39 (dt, 1H, J1=7.3, J2=16.9 Hz), 2.25 (dt, 1H, J1=7.3 Hz, J2=16.9 Hz), 1.45 (m, 1H), 1.23 (sx, 1H, J=7.4 Hz), 1.07 (d, 3H, J=6.9 Hz), 0.85 (t, 3H, J= 7.3 Hz); 13C NMR (75.5 MHz, CDCl3) δ214.4, 139.8, 128.9, 128.3, 126.2, 48.1, 41.7, 39.1, 25.6, 22.3, 16.5, 13.9; FTIR (neat film) cm-1 3028 (w), 2959 (s), 2932 (s), 2873 (m), 1947 (w), 1878 (w), 1805 (w), 1712 (s), 1604 (w), 1496 (w), 1454 (m), 1406 (w), 1375 (m), 1130 (w), 1032 (w), 992 (w), 746 (m), 700 (s).

EXAMPLE 36

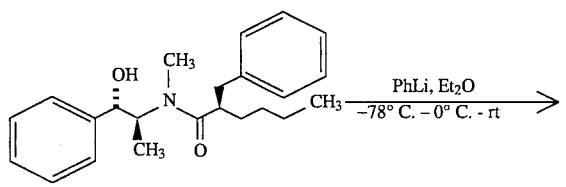

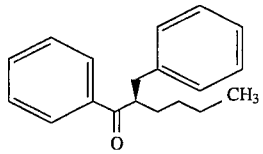

R-2-butyl-1,3-diphenyl-1-propanone

To a flame-dried 100 mL round-bottomed flask equipped with magnetic stir bar was added [1S-[1R*(S*), 2R*]]-α-butyl-N-( 2-hydroxy-1-methyl-2-phenylethyl)-N-methyl benzenepropionamide (1.0860 g, 3.1 mmol, 1.0 equiv.). The amide was azeotropically dried under reduced pressure as a solution with toluene (10 mL) and the reaction flask flushed with dry argon. Diethyl ether (30 mL) was added to the residue and the resulting solution cooled to −78° C. Phenyllithium (3.8 mL, 1.94M, 7.4 mmol, 2.4 equiv.) was added via syringe and the mixture warmed initially to 0° C. (10 min) and then to 23° C. TLC (50% ethyl acetate/hexanes) analysis of the mixture at this point showed no starting material. The mixture was cooled again to 0° C. and diisopropylamine (0.43 mL, 3.1 mmol, 1.0 equiv.) added to the mixture, followed 15 min later by 10% acetic acid/diethyl ether (10 mL). The mixture was extracted with water (50 mL) and the aqueous phase back extracted with ethyl acetate (50 mL) and dichloromethane (2×50 mL). The combined organic phases were dried over anhydrous sodium sulfate, decanted, and concentrated under reduced pressure. Flash chromatography (3–5% ethyl acetate/hexanes) of this concentrate then afforded R-2-butyl-1,3-diphenyl-1-propanone (0.7704 g, 94% yield) as a slightly yellow oil: 1H NMR (300 MHz, CDCl3) δ7.1–7.9 (m, 10H), 3.74 (m, 1H), 3.10 (dd, 1H, J1=7.7 Hz, J2=13.6 Hz), 2.78 (dd, 1H, J1=6.5 Hz, J2= 13.6 Hz), 1.80 (m, 1H), 1.55 (m, 1H), 1.25 (m, 4H), 0.80 (m, 3H); 13C NMR (75.5 MHz, CDCl3) δ204.0, 140.0, 137.5, 132.8, 129.0, 128.5, 128.3, 128.1, 126.1, 48.3, 38.2, 32.1, 29.5, 22.8, 13.9; FTIR (neat film) cm-1 3062 (w), 3027 (m), 2955 (s), 2870 (m), 1961 (w), 1898 (w), 1812 (w), 1679 (s), 1596 (m), 1581 (w), 1495 (m), 1452 (s), 1374 (w), 1230 (s), 1204 (m), 1179 (w), 1075 (w), 1002 (w), 946 (m), 751 (m), 699 (S).

EXAMPLE 37

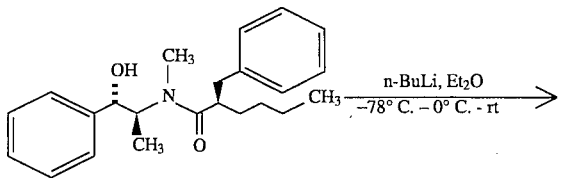

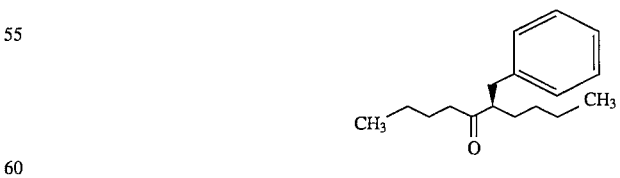

R-2-butyl-1-phenyl-3-heptanone

To a flame-dried 100 mL round-bottomed flask equipped with magnetic stir bar was added [1S-[1R*(S*), 2R*]]-α-butyl-N-( 2-hydroxy-1-methyl-2-phenylethyl)-N-methyl benzenepropionamide (1.0012 g, 2.8 mmol, 1.0 equiv.). The amide was azeotropically dried under reduced pressure as a solution with toluene (10 mL) and the reaction flask flushed with dry argon. Diethyl ether (30 mL) was added to the residue and the resulting solution cooled to −78° C. n-Butyllithium (3.5 mL, 1.71M, 6.0mmol, 2.1 equiv.) was added via syringe and the mixture warmed initially to 0° C. (5 min) and then to 23° C. TLC (50% ethyl acetate/hexanes) analysis of the mixture at this point showed no starting material. The mixture was cooled again to 0° C. and diisopropylamine (0.40 mL, 2.8 mmol, 1.0 equiv.) added to the mixture, followed 15 min later by 10% acetic acid/diethyl ether (10 mL). The mixture was extracted with water (30 mL) and the aqueous phase back extracted with ethyl acetate (30 mL) and dichloromethane (2×30 mL). The combined organic phases were dried over anhydrous sodium sulfate, decanted, and concentrated under reduced pressure. Flash chromatography (2.5–10% ethyl acetate/hexanes) of this concentrate then afforded R-2-butyl-1-phenyl-3-heptanone (0.6518 g, 94% yield) as a slightly yellow oil: 1H NMR (300 MHz, CDCl3) δ7.20 (m, 5H), 2.80 (m, 2H), 2.65 (dd, 1H, J1=5.0 Hz, J2=12.0 Hz), 2.28 (dt, 1H, J1=7.3 Hz, J2=17.2 Hz), 2.11 (dt, 1H, J1=7.3 Hz, J2=17.2 Hz), 1.65 (m, 1H), 1.40 (m, 3H), 1.25 (m, 6H), 0.87 (t, 3H, J=7.0 Hz), 0.81 (t, 3H, J=7.3 Hz); 13C NMR (75.5 MHz, CDCl3) δ214.6, 139.9, 128.9, 126.1, 54.0, 43.4, 38.2, 31.6, 29.5, 25.2, 22.8, 22.2, 13.9, 13.8; FTIR (neat film) cm-1 3028 (m), 2957 (s), 2872 (s), 1944 (w), 1874 (w), 1803 (w), 1712 (s, C=O), 1604 (w), 1496 (m), 1455 (s), 1405 (w), 1378 (m), 1255 (w), 1216 (w), 1126 (w), 1055 (w), 1030 (w), 973 (w), 748 (m), 700 (s).

EXAMPLE 38

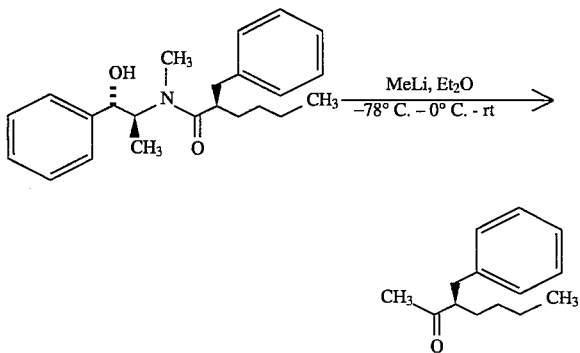

R-3-(phenylmethyl)-2-heptanone

To a flame-dried 100 mL round-bottomed flask equipped with magnetic stir bar was added [1S-[1R*(S*), 2R*]]-α-butyl-N-( 2-hydroxy-1-methyl-2-phenylethyl)-N-methyl benzenepropionamide (1.0303 g, 2.9 mmol, 1.0 equiv.). The amide was azeotropically dried under reduced pressure as a solution with toluene (10 mL) and the reaction flask flushed with dry argon. Diethyl ether (30 mL) was added to the residue and the resulting solution cooled to 0° C. Methyllithium (6.2 mL, 1.3M, 8.1 mmol, 2.8 equiv.) was added via syringe and the mixture warmed to 23° C. TLC (50% ethyl acetate/hexanes) analysis of the mixture at this point showed no starting material. The mixture was cooled again to 0° C. and diisopropylamine (0.41 mL, 2.9 mmol, 1.0 equiv.) added to the mixture, followed 15 min later by 10% acetic acid/diethyl ether (10 mL). The mixture was extracted with water (20 mL) and the aqueous phase back extracted with ethyl acetate (20 mL) and dichloromethane (2×20 mL). The combined organic phases were dried over anhydrous sodium sulfate, decanted, and concentrated under reduced pressure. Flash chromatography (15% ethyl acetate/hexanes) of this concentrate then afforded R-3-(phenylmethyl)-2-heptanone (0.5817 g, 98% yield) as a slightly yellow oil: 1H NMR (300 MHz, CDCl3) δ7.2 (m, 5H), 2.85 (m, 2H), 2.69 (dd, 1H, J1= 5.1 Hz, J2=12.1 Hz), 2.00 (s, 3H), 1.65 (m, 1H), 1.45 (m, 1H), 1.27 (m, 4H), 0.88 (t, 3H, J=6.9 Hz); 13C NMR (75.5 MHz, CDCl3) δ212.5, 139.6, 128.8, 128.4, 126.2, 54.7, 37.9, 31.4, 30.2, 29.4, 22.7, 13.9; FTIR (neat film) cm-1 3027 (m), 2931 (s), 2858 (s), 1713 (s), 1603 (w), 1496 (m), 1455 (s), 1351 (m), 1162 (m), 1741 (m), 700 (s), 505 (w).

Method—Analysis of diastereomeric or enantiomeric excesses of alkylated amides, carboxylic acids, alcohols, aldehydes, or ketones The diastereomeric purity of the alkylated amides was analyzed by chiral GC analysis of the corresponding trimethylsilyl ether derivatives. The enantiomeric purity of the carboxylic acids was determined by GC analysis of the amides derived by coupling the acids with (R)-(+)-α-methylbenzylamine. The enantiomeric purity of the alcohols was determined by coupling the alcohol with (S)-α-methoxy-α-(trifluoromethyl)phenylacetyl chloride to form the Mosher ester, and analyzing the ratio by NMR. The enantiomeric purity of the aldehydes was determined either by lithium aluminum hydride or diisobutylaluminum hydride reduction of the aldehyde to the alcohol followed by formation of the Mosher ester, or oxidation of the aldehyde to the carboxylic acid with sodium chlorite, and coupling with (R)-(+)-α-methylbenzylamine. The enantiomeric purity of the ketones was determined by lithium aluminum hydride or diisobutylaluminum hydride reduction to the alcohol, followed by formation of the Mosher ester.

A general procedure for generating the trimethylsilyl ether of the alkylated amides is as follows. A dry 10 mL flask equipped with a magnetic stirrer was charged with the alkylated amide (0.1 mmol, 1.0 equiv), and the amide was dissolved in dichloromethane (1.0 mL). Triethylamine (0.3 mmol, 3.0 equiv) and chlorotrimethylsilane (0.2 mmol, 2.0 equiv) were added, and the reaction was stirred at 23° C. for several hours. The reaction was quenched with water, and the trimethylsilyl ether was extracted with ethyl acetate.

A general procedure for coupling a carboxylic acid with (R)-(+)-α-methylbenzylamine is as follows. A dry 10 mL flask equipped with a magnetic stirrer was charged with the acid (0.18 mmol, 1.0 equiv), (R)-(+)-α-methylbenzylamine (0.25 mmol, 1.4 equiv), 1-hydroxybenzotriazole (0.31 mmol, 1.7 equiv), and dimethylformamide (0.6 mL). 1-(3-Dimethylaminopropyl)- 3-ethylcarbodiimide hydrochloride (0.31 mmol, 1.7 equiv) and triethylamine (0.82 mmol, 4.5 equiv), were added and the reaction was stirred overnight at 23° C. The reaction was quenched with 1N HCl, and the amide was extracted from 1N HCl with ethyl acetate.

A general procedure for coupling an alcohol with Mosher chloride is as follows. A dry 10 mL flask equipped with a magnetic stirrer was charged with α-methoxy-α (trifluoromethyl) phenylacetic acid (0.23 mmol, 2.7 equiv), and the acid was azeotropically dried with benzene (2 mL). The residue was dissolved in dichloromethane (1 mL), and oxalyl chloride (0.19 mmol, 2.3 equiv) and dimethylformamide (catalytic amount) were added, and the mixture was stirred at 23° C. for 1 hour. The mixture was transferred via cannula into a mixture of dichloromethane (1 mL), the alcohol (0.08 mmol, 1.0 equiv), and activated 3 A molecular sieves, and the mixture was stirred overnight at 23° C. (more equivalents of the Mosher chloride are often required for complete reaction of alcohols derived from the ketones). The reaction mixture was dissolved in ethyl acetate, and extracted with saturated sodium bicarbonate and then 1N HCl or saturated ammonium chloride.

A general procedure for aldehyde reduction is as follows. A dry 10 mL flask equipped with a magnetic stirrer was charged with the aldehyde (0.15 mmol, 1.0 equiv), tetrahydrofuran (1.0 mL), and cooled to −78° C. Diisobutylaluminum hydride (0.5 mmol, 3.4 equiv) was added, and the reaction was warmed to 0° C. The reaction was stirred at 0° C. for 20 minutes and quenched with 1N HCl, and the product was extracted from 1N HCl with 1:1 ethyl acetate/hexanes, dried, concentrated, and chromatographed.

A general procedure for aldehyde oxidation is as follows. A 10 mL flask equipped with a magnetic stirrer was charged with the aldehyde (0.20 mmol, 1.0 equiv), tert-butanol (4 mL), and 2-methyl-2-butene (2.0M in tetrahydrofuran, 1.0 mL, 10 equiv). The oxidant was prepared by dissolving sodium chlorite (1.9 mmol, 9.7 equiv) and sodium dihydrogen phosphate (1.44 mmol, 7.4 equiv) in water (2 mL), and pipeting this solution into the aldehyde mixture. The biphasic mixture was stirred vigorously at 23° C. for approximately 1 hour, extracted with dilute sodium bicarbonate, acidified to pH=2, and extracted with ethyl acetate.

A general procedure for ketone reduction is as follows. A dry 10 mL flask equipped with a magnetic stirrer was charged with the ketone (0.46 mmol, 1.0 equiv) and ether (1 mL), and cooled to 0° C. Lithium aluminum hydride (1.0M in ether, 0.7 mL, 1.5 equiv) was added, and the mixture was warmed to 23° C. The reaction was stirred for 1 hour, quenched with water, and extracted with dichloromethane.

It should be understood that the examples merely serve to illustrate the invention, and are not intended to limit or otherwise define it. Applicant's invention is defined according to the claims which follow.

I claim:

1. A compound of the formula

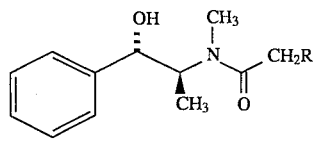

or

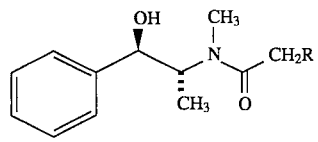

wherein R is a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from a $C_1$–$C_{14}$ straight or branched-chain alkyl group, a $C_2$–$C_{14}$ straight or branched-chain alkenyl or alkynyl group, halo, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl, provided that R is not 1-(S)-methylpentyl or (R)-α-methylbenzyl.

2. A compound according to claim 1 wherein R is methyl, n-butyl, phenyl or benzyl.

3. A compound of the formula

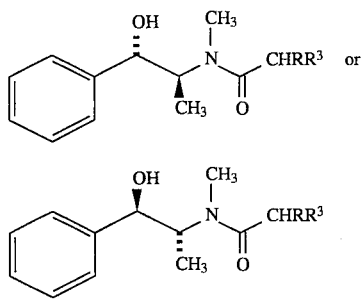

wherein R and $R^3$ are different and are each independently a $C_1$–$C_{14}$ straight or branched-chain alkyl group, a $C_2$–$C_{14}$ straight or branched-chain alkenyl or alkynyl group, $C_1$–$C_6$ alkoxy, $C_1$–$C_6$ alkylthio, halo, hydroxy, heteroaryl, $C_3$–$C_8$ cycloalkyl, $C_9$–$C_{16}$ bicycloalkyl, aryl or $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl where the alkyl, alkenyl, alkynyl, alkoxy, alkylthio, heteroaryl, cycloalkyl, bicycloalkyl and aryl are optionally substituted with one or more groups independently selected from a $C_1$–$C_{14}$ straight or branched-chain alkyl group, a $C_2$–$C_{14}$ straight or branched-chain alkenyl or alkynyl group, halo, $C_1$–$C_6$ alkylthio, heteroaryl, $C_3$–$C_8$ cycloalkyl, $C_9$–$C_{16}$ bicycloalkyl, aryl, hydroxy, $C_1$–$C_6$ alkoxy, thio, $C_1$–$C_6$ alkylthio, $NR^1R^2$ where $R^1$ and $R^2$ are each independently selected from the group consisting of hydrogen, $C_1$–$C_6$ straight or branched-chain alkyl, $C_3$–$C_8$ cycloalkyl, $CO_2R^4$ and $NHCO_2R^4$ where $R^4$ is $C_1$–$C_{14}$ straight or branched-chain alkyl.

\* \* \* \* \*